(12) United States Patent
Douglas et al.

(10) Patent No.: US 6,743,771 B2
(45) Date of Patent: Jun. 1, 2004

(54) METHODS AND COMPOSITIONS FOR CONTROLLING PROTEIN ASSEMBLY OR AGGREGATION

(75) Inventors: Michael G. Douglas, St. Louis, MO (US); Avinash N. Amin, St. Louis, MO (US)

(73) Assignee: Novactyl, Inc., St. Louis, MO (US)

( * ) Notice: Subject to any disclaimer, the term of this patent is extended or adjusted under 35 U.S.C. 154(b) by 50 days.

(21) Appl. No.: 09/904,987

(22) Filed: Jul. 12, 2001

(65) Prior Publication Data

US 2002/0037908 A1 Mar. 28, 2002

Related U.S. Application Data

(63) Continuation-in-part of application No. 09/677,500, filed on Oct. 2, 2000, now Pat. No. 6,407,125, which is a continuation-in-part of application No. 09/657,554, filed on Sep. 8, 2000, now Pat. No. 6,579,891, which is a continuation-in-part of application No. 09/657,989, filed on Sep. 8, 2000, now Pat. No. 6,410,570, which is a continuation-in-part of application No. 09/127,620, filed on Aug. 1, 1998, now Pat. No. 6,127,393, which is a continuation-in-part of application No. 08/843,157, filed on Apr. 11, 1997, now abandoned, which is a continuation-in-part of application No. 08/581,351, filed on Dec. 29, 1995, now Pat. No. 5,767,135.

(60) Provisional application No. 60/024,221, filed on Oct. 22, 1996, and provisional application No. 60/026,992, filed on Sep. 20, 1996.

(51) Int. Cl.[7] .................. A61K 38/00; A61K 31/535; C07K 14/00

(52) U.S. Cl. .................. 514/2; 514/228.8; 530/388.9; 530/389.8

(58) Field of Search ................ 436/15, 176; 514/228.8, 514/2; 604/48; 530/388.9, 389.8

(56) References Cited

U.S. PATENT DOCUMENTS

| | | | |
|---|---|---|---|
| 3,903,285 A | 9/1975 | Umezawa et al. | 424/266 |
| 4,044,140 A | 8/1977 | Sherlock | 424/266 |
| 4,120,762 A | 10/1978 | Sviokla | 204/2 |
| 4,138,488 A | 2/1979 | Sherlock et al. | 424/250 |
| 4,139,625 A | 2/1979 | Sherlock et al. | 424/266 |
| 4,293,547 A | 10/1981 | Lewis et al. | 424/180 |
| 4,443,459 A | 4/1984 | Yano et al. | 424/266 |
| 4,814,351 A | 3/1989 | Mathews et al. | 514/566 |
| 5,057,320 A | 10/1991 | Evans et al. | 424/447 |
| 5,157,046 A | 10/1992 | Van Wauwe et al. | 514/397 |
| 5,164,414 A | 11/1992 | Vincent et al. | 514/563 |
| 5,173,486 A | 12/1992 | Monkovic et al. | 514/211 |
| 5,219,847 A | 6/1993 | Taguchi et al. | 514/188 |
| 5,284,840 A | 2/1994 | Rupprecht et al. | 514/183 |
| 5,391,537 A | 2/1995 | Takabe et al. | 504/243 |
| 5,403,816 A | 4/1995 | Takabe et al. | 504/243 |
| 5,484,951 A | 1/1996 | Kun et al. | 549/285 |
| 5,516,941 A | 5/1996 | Kun et al. | 564/166 |
| 5,536,743 A | 7/1996 | Borgman | 514/39.8 |
| 5,767,135 A | 6/1998 | Fernandez-Pol | 514/354 |
| 6,001,555 A | 12/1999 | Henderson et al. | 435/5 |
| 6,083,758 A | 7/2000 | Imperiali et al. | 436/73 |
| 6,127,393 A | 10/2000 | Fernandez-Pol | 514/354 |

OTHER PUBLICATIONS

Quaternary structure (labeled REF 1) from "Structure and Function of Macromolecules" University of Paisley.*

Peptide bond and peptides (labeled REF 2) from "Structure and Function of Macromolecules" University of Paisley.*

Fernandez–pol, J. A. et al. (2001) Antiviral, cytotoxic and apoptotic activities of picolinic acid on human immunodeficiency virus–1 and human herpes simplex virus–2 infected cells. Anticancer Res. vol. 21, pp. 3773–3776.*

Cockhill, J., et al., Action of Picolinic acid and Structurally related pyridine carboxylic acids on quinolinic acid–induced cortical cholinergic damage, Brain Research, 1992, No. 599 (1), pp. 57–63.

Chemical Abstracts, Skin–lightening preparations containing fusaric acids and/or picolinic acids, 1990, Abstract No., 217815f, p. 359.

Collins, J. J., et al. Transient Growth Inhibition of *Escherichia coli* K–12 by Ion Chelators: "In Vivo" Inhibition of Ribonucleic Acid Synthesis; Journal of Bacteriology, Jun. 1979, vol. 138, No. 3, pp. 923–932.

Rein, A., et al., Inactivation of Murine Leukemia virus by Compounds That React with the Zinc Finger in the Viral Nucleocapsid Protein, Journal of Virology, Aug. 1996, pp. 4966–4972.

Medline Abstract, Wunderlich, V., et al., Disintegration of retroviruses by chelating agents, Archives of Virology, Medline Accession No. 83073940, 1982, 73 (2), pp. 171–183.

Medline Abstract, Xu, B., et al.; Efficacy of bimolane in the Malessezia ovalis model of psoriasis; Journal of Dermatology, Medline Accession No. 92218737, Dec. 1991, 18 (12), pp. 707–713.

(List continued on next page.)

*Primary Examiner*—Karen Cochrane Carlson
*Assistant Examiner*—Samuel W. Liu

(57) ABSTRACT

Compositions and methods for controlling prepathological and pathological protein assembly or aggregation using picolinic acid, analogs, or derivatives thereof are described. The compositions of the invention, capable of solubilizing a conformationally altered protein, comprise a carboxylic acid anion of picolinic acid, its analogs, or derivatives thereof and a cation. According to the methods of the invention, conformationally altered protein assembly or aggregation in an animal is prevented or reversed by introducing the compositions of the invention to the conformationally altered protein. The compositions can be administered systemically by injection, oral administration, inhalation, transdermal, or other routes of administration. The compositions and methods can be used to treat diseases manifested by conformationally altered protein assembly or aggregation including, but not limited to Alzheimer's disease, spongiform encephalopathy, cerebral amyloid angiopathy, Parkinson's disease, frontal temporal dementia, Pick's disease, amyotrophic lateral sclerosis, Huntington's disease and Creutzfelds-Jakob disease.

27 Claims, 11 Drawing Sheets

OTHER PUBLICATIONS

Medline Abstract, Oxford, J. S., et al.; Potential target sites for antiviral inhibitors of human immunodeficiency virus (HIV), Journal of Antimicrobial Chemotherapy, Medline Accession No., 89234021, Jan. 1989, 23 Suppl A 9–27, Ref. 75.

Medline Abstract, Edelman D. A, et al.; Treatment of bacterial vaginosis with intervaginal sponges containing metronidazole, Journal of Reproductive Medicine, Medline Accession No., 89279809, May 1989, 34 (5), pp. 341–344.

Fernandez–Pol, J. A., Growth Factors, Oncogenes and Aging, Comprehensive Geriatric Oncology, Apr. 21, 1997, pp. 179–196.

Evans, G. W., An Inexpensive, Convenient Adjunct for the Treatment of Diabetes, Letter to the Editor, The Western Journal of Medicine, Nov. 1991, p. 549.

Wang, X., A chelate theory for mechanism of action of aspirin–like drugs; Medical Hypotheses, 1998, No. 50, pp. 239–251.

Brem; S., Angiogenesis and Cancer Control: From Concept to Therapeutic Trial, Cancer Control, Sep./Oct. 1999, vol. 6, No. 5, pp. 436–458.

Turpin, J. A., et al., Inhibitors of Human Immunodeficiency Virus Type 1 Zinc Fingers Prevent Normal Processing of Gag Precursors and Result in the Release of Noninfectious Virus Particles, Journal of Virology, Sep. 1996, vol. 70, No. 9, pp. 6180–6189.

Medline Abstract, Kalisch, B. E., et al.; Picolinic acid protects against quinolinic acid–induced depletion of NADPH diaphorase containing neurons in the rat striatum, Brain Research, Medline Accession No. 95219467, Dec. 30, 1994, 668 (1–2) pp. 1–8.

Medline Abstract, Ensoli, B., et al., Tat protein of HIV–1 stimulates growth of cells derived from Kaposi's sarcoma lesions of AIDS patients, Nature, Medline Accession No 90231470, May 3, 1990, 345 (6270), pp. 84–86.

Komatsu, H., et al., Viral RNA Binding Properties of Human Immunodeficiency Virus Type–2 (HIV 2) Nucleocapsid Protein–Derived Synthetic Peptides, Biochemistry and Molecular Biology International, May 1996, vol. 38, No. 6, pp. 1143–1154.

Rice, W. G., et al., Inhibitors of HIV Nucleocapsid Protein Zinc Fingers as Candidates for the Treatment of AIDS, SCIENCE, Nov. 17, 1995, Vol 270, pp. 1194–1197.

Hathout, Y., et al., Characterization of Intermediates in the Oxidation of Zinc Fingers In Human Immunodeficiency Virus Type 1 Nucleocapsid Protein P7, Drug Metabolism and Disposition, 1996, vol. 24, No. 12, pp. 1395–1400.

Von Weizsacker, F., et al., Gene Therapy for Chronic Viral Hepatitis: Ribozymes, Antisense Oligonucleotides, and Dominant Negative Mutants, HEPATOLOGY, Aug. 1997, pp. 251–255.

Smart, T., Zinc Fingers: The Next Antiviral Target?, GNMC Treatment Issues, Oct. 1995.

Fuchs, C. K., HIV Finger Therapeutics Screening and Development Opportunity, Article from Aug. 1995 Antiviral Agents Bulletin.

Octamer, Inc., Ronald Brown, President, About Octamer, date: as early as 1995.

Priel, E., et al., DNA binding properties of the zinc–bound and zinc–free HIV nucleocapsid protein: supercoiled DNA unwinding and DNA–protein cleavable complex formation, FEBS Letters, 1995, No. 362, pp. 59–64.

Rein, A., et al., Evidence that a Central Domain of Nucleocapsid Protein Is Required for RNA Packaging in Murine Leukemia Virus, Journal of Virology, Sep. 1994, vol. 68, No. 9, pp. 6124–6129.

Otsuka, M., et al., Novel Zinc Chelators Which Inhibit the Binding of HIV–EP1 (HIV Enhancer Binding Protein) to NF–KB Recognition Sequence, J. Med Chem., 1994, No. 37, pp. 4267–4269.

Gorelick, R. J., et al., Genetic Analysis of the Zinc Finger in the Moloney Murine Leukemia Virus Nucleocapsid Domain: Replacement of Zinc–Coordinating Residues with Other Zinc–Coordinating Residues Yields Noninfectious Particles Containing Genomic RNA, Journal of Virology, Apr. 1996, vol. 70, No. 4, pp. 2593–2597.

Rice, R. G., et al., Inhibition of HIV–1 infectivity by zinc–ejecting aromatic C–nitroso compounds, NATURE, Feb. 4, 1993, Vol 361, pp. 473–475.

Condra, J. H., et al., Preventing HIV–1 Drug Resistance, Science & Medicine, Jan. Feb. 1997, pp. 14–23.

Tummino, P. J., et al., The in vitro ejection of zinc from human immunodeficiency virus (HIV) type 1 nulcleocapsid protein by disulfide benzamides with cellular anti–HIV activity, Proceedings of the National Academy of Sciences, Feb. 1996, vol. 93, pp. 969–973.

Bess, J. W. Jr. et al., Tightly Bound Zinc in Human Immunodeficiency Virus Type 1, Human T–Cell Leukemia Virus Type 1, and Other Retroviruses, Journal of Virology, Feb. 1992, vol. 66, No. 2, pp. 840–847.

Berg, J. M., Zinc Fingers and Other Metal–binding Domains The Journal of Biological Chemistry, Apr. 25, 1990, vol. 265, No. 12, pp. 6513–6516.

Berg, J. M, Potential Metal–Binding Domains in Nucleic Acid Binding Proteins, SCIENCE, Apr. 25, 1986, vol. 232, pp. 485–487.

Mays, Thomas D., National Institute of Health, Federal Register Notices, Aug. 10, 1995, vol. 60, No. 154.

Fernandez–Pol, J. A., et al., Cytotoxic Activity of Fusaric Acid on Human Adenocarcinoma Cells in Tissue Culture; Anticancer Research, 1993, No. 13, pp. 57–64.

Beninger, R. J., et al., Picolinic Acid Blocks The Neurotoxic But Not The Neuroexcitant Properties Of Quinounic Acid In The Rat Brain: Evidence From Turning Behavior An Tyrosine Hydroxylase Immunohistochemistry, Neuroscience, 1994, vol. 61, No. 3, pp. 603–612.

Clancy, S. P., et al., Effects of Chromium Picolinate Supplementation on Body Composition, Strength, and Urinary Chromium Loss in Football Players; Original Research, International Journal of Sport Nutrition, 1994, vol. 4, pp. 142–153.

Lee, N. A., et al., Beneficial Effect of Chromium Supplementation on Serum Triglyceride Levels in NIDDM, Diabetes Care, Dec. 1994, vol. 17 No. 12, pp. 1449–1452.

Page, T. G., et al., Effect of Chromium Picolinate on Growth and Serum and Carcass Traits of Growing–Finishing Pigs [1,2,3], J. Anim. Sci, 1993, No. 71, pp. 656–662.

Lindemann, M. D., et al., Dietary Chromium Picolinate Additions Improve Gain: Feed and Carcass Characteristics in Growing–Finishing Pigs and Increase Litter Size in Reproducing Sows, J. Anim. Sci., 1995, No. 73, pp. 457–465.

Evans, G. W., et al., Chromium Picolinate Increases Membrane Fluidity and Rate of Insulin Internalization, Journal of Inorganic Biochemistry, 1992, No. 46, pp. 243–250.

Evans, G. W., et al., Composition and Biological Activity of Chromium–Pyridine Carboxylate Complexes, Journal of Inorganic Biochemistry, 1993, No. 49, pp. 177–187.

Fernandez–Pol, J. A., et al., Control of growth by picolinic acid: Differential response of normal and transformed cells; Cell Biology; Jul. 1977, vol. 74, No. 7, pp. 2889–2893.

Fernandez–Pol, J. A., Isolation and Characterization of a Siderophore–Like Growth Factor from Mutants of SV40–Transformed Cells Adapted to Picolinic Acid, Cell, Jul. 1978, vol. 14, pp. 489–499.

Fernandez–Pol, J. A., Growth Factors, Oncogenes, Antioncogenes and Aging, Geriatric Oncology, 1992, Chapter 7, pp. 60–75.

Fernandez–Pol, J. A., Morphological Changes Induced by Picolinic Acid in Cultured Mammalian Cells; Experimental and Molecular Pathology, 1978, No. 29, pp. 348–357.

Johnson, G. S., et al., NRK Cells Synchronized In $G_1$ By Picolinic Acid Are Super–Sensitive To Prostaglandin $E_1$ Stimulation, FEBS Letters, Mar. 1977, vol. 74, No. 2; pp. 201–204.

Fernandez–Pol, J. A., Peptide and Protein Complexes of Transition Metals as Modulators of Cellular Replication; International Journal of Nuclear Medicine and Biology, 1981, vol. 8., pp. 231–235.

Fernandez–Pol, J. A.,et al., Iron Transport In NRK Cells Synchronized In $G_1$ By Picolinic Acid, Cell Biology International Reports, 1978, vol. 2, No. 5, pp. 433–439.

Fernandez–Pol, J. A., Iron: Possible Cause of the $G_1$ Arrest Induced In NRK Cells By Picolinic Acid; Biochemical And Biophysical Research Communications, 1977, vol 78, No. 1, pp. 136–143.

Fernandez–Pol, J. A., Transition Metal Ions Induce Cell Growth In NRK Cells Synchronized In $G_1$ By Picolinic Acid, Biochemical And Biophysical Research Communications, 1977, vol. 76, No. 2, pp. 413–419.

Fernandez–Pol, J. A., et al., Selective Toxicity Induced by Picolinic Acid in Simian Virus 40–transformed Cells in Tissue Culture, Cancer Research, Dec. 1977, No. 37, pp. 4276–4279.

Gargas, M. L., et al., Urinary Excretion of Chromium by Humans Following Ingestion of Chromium Picolinate, Drug Metabolism and Disposition, 1994, vol. 22, No. 4, pp. 522–529.

Letter to the Editor, Chromium Picolinate is an Efficacious and Safe Supplement, International Journal of Sport Nutrition, Human Kinetics Publishers Inc.,1993, No. 3., pp. 117–122.

Boegman, R. J. et al., Neurotoxicity of Tryptophan Metabolities, Annals New York Academy of Sciences, 1990, vol. 585, pp. 261–273.

Press, R. I., et al., The Effect of Chromium Picolinate on Serum Cholesterol and Apoliprotein Fractions in Human Subjects, West J. Med., Jan. 1990, No. 152, pp. 41–45.

Shapiro, A., et al., In Vivo and In Vitro activity by Diverse Chelators against *Trypanosoma brucei brucei*, The Journal of Protozoology, Feb. 1982, Vol 29, No. 1, pp. 85–90.

Web site: http://www.ncbi.nlm.nih.gov; National Center for Biotechnology Information, National Library of Medicine, National Institute of Health, Revised Jul. 10, 2001.

Fernandez–Pol, J.A., Hamilton, P.D., and Klos, D.J., "Essential Viral and Cellular Zinc and Iron Containing Metalloproteins as Targets for Novel Antiviral and Anticancer Agents: Implications for Prevention and Therapy of Viral Diseases and Cancer", Anticancer Research 21:931–958 (2001).

Prusiner, S.B., "The Prion Diseases", from http://www.albany.net/~tjc/prion.html; pp. 1–20, © copyright 1998, 1999, 2000, 2001.

Patent Abstracts of Japan, Skin Drug for External Use, Publication No. 02164808, Jun. 25, 1990, Application Date Dec. 15, 1988, Application No. 63317533.

Derwent Publications, New trypsin inhibitor for treatment of gastric ulcer, pancreatitis and dermatitis, Abstract No. 94–185855, Date Apr. 19, 1994.

Ruffman, R. et al., Antiproliferative Activity of Picolinic Acid Due to Macrophage Activation, 1987, pp. 607–614.

Varadinova, T. L., et al., Mode of action of Zn–Complexes on Herpes Simplex Virus Type I Infection In Vitro, Journal of Chemotherapy, 1993, vol. 5, n. 1, pp. 3–9.

Blasi, E., et al., Protective Effect of Picolinic Acid on Mice Intracerebrally Infected with Lethal Doses of *Candida albicans*; Antimicrobial Agents and Chemotherapy, Nov. 1993, vol. 37, No. 11, pp. 2422–2426.

Melillo, G., et al., Regulation of Nitric–oxide Synthase mRNA Expression by Interferon–$\gamma$ and Picolinic Acid, The Journal of Biological Chemistry Mar. 18, 1994 Vol 269, No. 11, pp. 8128–8133.

Blasi, E., et al., Inhibition of Retroviral mRNA Expression In The Murine Macrophage Cell Line GG2EE by Biologic Response Modifiers, The Journal of Immumology, Sep. 15, 1988, Vol 141, No. 6, pp. 2153–2157.

Mikogami, T., et al., Effect of intracellular iron depletion by picolinic acid on expression of the lactoferrin receptor in the human colon carcinoma cell subclone HT29–18–$C_1$, Biochem J. (1995) 308, pp. 391–397 (Printed in Great Britain).

Cox, G. W., et al., IL–4 Inhibits the Costimulatory Activity of IL–2 Or Picolinic Acid But Not Of Lipopolysaccharide on IFN–$\gamma$–Treated Macrophages; The Journal of Immunology, Dec. 1, 1991, vol. 147, No. 11, pp. 3809–3814.

Blasi, E., et al., Pattern of cytokine gene expression in brains of mice protected by picolinic acid against lethal intracerebral infection with *Candida albicans*; Journal of Neuroimmunology 52, 1994, pp. 205–213.

Melillo, G., et al., Picolinic Acid, a Catabolite of L–Tryptophan, Is a Costimulus for the Induction of Reactive Nitrogen Intermediate Production in Murine Macrophages, The Journal of Immunology, May 1, 1993, Vol 150, No. 9, pp. 4031–4040.

Bode, A. M., et al., Inhibition of glucose–6–phosphate phosphohydrolase by 3–mercaptopicolinate and two analogs is metabolically directive, Biochem Cell Biol, 1993, Vol 71, pp. 113–121.

Vrooman, L., et al., Picolinic Acid modulates kainic acid–evoked glutamate release from the striatum in vitro; Brain Research, 1993, vol. 627, pp. 193–198.

Varesio, L., et al., Ribosomal RNA Metabolism in Macrophages, Current Topics In Microbiology and Immunology, 1992, vol. 181, pp. 209–237.

Frankel, A. D. et al., Cellular Uptake of the Tat Protein from Human Immunodeficiency Virus, Cell, Dec. 23, 1988, vol. 55, pp. 1189–1193.

Xynos, F. P., et al., Expression of Metallopanstimulin in Condylomata Acuminata of the Female Anogenital Region Induced by Papilloma Virus, Anticancer Research, 1994, vol. 14, pp. 773–786.

Bobilya, D. J., et al., Ligands Influence Zn Transport into Cultured Endothelial Cells, Society for Experimental Biology and Medicine, 1993, pp. 159–166.

Tarbell, D.S., Yamamoto, Y. & Pope, B.M. *Proc. Natl. Acad. Sci. USA,* 69, No. 3, pp 730–732, Mar. 1972.

Glenner, G. G., and Wong, C. W., *Biochem. Biophys. Res. Commun.,* vol. 120, No. 3, May 16, 1984.

Serpell, L. C., Blake, C.C.F., and Fraser, P.E., "Molecular Structure of a Fibrillar Alzheimer's Aβ Fragment", *Biochemistry* 2000, 39, 13269–13275.

Hirakura, Y., Yiu, W.W., Yamamoto, A., and Kagan, B.L., "Amyloid peptide channels: blockade by zinc and inhibition by Congo red (amyloid channel block)", *Amyloid* 2000 Sep; 7(3): 194–9.

Yang, D., McLaurin, J., Qin, K., Westaway, D., and Fraser, P.E., Examining the zinc binding site of the.

* cited by examiner

FIG. 1
(SEQ. ID NO. 1)

AspAlaGluPheArgHisAspSerGlyTyrGluValHisHisGlnLysLeuValPhePheAlaGluAspValGlySerAsnLysGlyAla
IleIleGlyLeuMetValGlyGlyValValIleAlaThr

FIG. 2
(SEQ. ID NO. 2)

MetLeuProGlyLeuAlaLeuLeuLeuLeuAlaAlaTrpThrAlaArgAlaLeuGluValProThrAspGlyAsnAlaGlyLeuLeuAlaGluP
roGlnIleAlaMetPheCysGlyArgLeuAsnMetHisMetAsnValGlnAsnGlyLysTrpAspSerAspProSerGlyThrLys
ThrCysIleAspThrLysGluGlyIleLeuGlnTyrCysGlnGluValTyrProGluLeuGlnIleThrAsnValValGluAlaAsnGlnProValT
hrIleGlnAsnTrpCysLysArgGlyArgLysGlnCysLysThrHisProHisPheValIleProTyrArgCysLeuValGlyGluPheValSerAs
pAlaLeuLeuValProAspLysCysLysPheLeuHisGlnGluArgMetAspValCysGluThrHisLeuHisTrpHisThr
ValAlaLysGluThrCysSerGluLysSerThrAsnLeuHisAspTyrGlyMetLeuLeuProCysGlyIleAspLysPheArgGlyValGluPh
eValCysCysProLeuAlaGluGluSerAspAsnValAspSerAlaAspAlaGluGluAspAspSerAspValTrpTrpGlyGlyAlaAspThr
AspTyrAlaAspGlySerGluAspLysValValGluValAlaGluGluGluValAlaGluValGluGluGluAlaAsp
AspAspGluAspAspGluAspGlyAspGluValGluGluGluAlaGluGluProTyrGluGluAlaThrGluArgThrThrSerIleAla
ThrThrThrThrThrThrThrGluSerValGluGluValValArgGluValCysSerGluGlnAlaGluThrGlyProCysArgAlaMetIleSer
ArgTrpTyrPheAspValThrGluGlyLysCysAlaProPhePheTyrGlyGlyCysGlyGlyAsnArgAsnAsnPheAspThrGluGluTyr
CysMetAlaValCysGlySerAlaMetSerGlnSerLeuLeuLysThrThrGlnGluProLeuAlaArgAspProValLysLeu
ProThrThrAlaAlaSerThrProAspAlaValAspLysTyrLeuGluThrProGlyAspGluAsnGluHisAlaHisPheGlnLysAla
LysGluArgLeuGluAlaLysHisArgGluArgMetSerGlnValMetArgGluTrpGluGluAlaGluArgGlnAlaLysAsnLeuProLys
AlaAspLysLysAlaValIleGlnHisPheGlnGluLysValGluSerLeuGluGlnGluAlaAlaAsnGluArgGlnGlnLeuVal
GluThrHisMetAlaArgValGluAlaMetLeuAsnAspArgArgArgLeuAlaLeuGluAsnTyrIleThrAlaLeuGlnAlaValPro
ProArgProArgHisValPheAsnMetLeuLysLysTyrValArgAlaGluGlnLysAspArgGlnHisThrLeuLysHisPheGluHis
ValArgMetValAspProLysLysAlaAlaGlnIleArgSerGlnValMetThrHisLeuArgValIleTyrGluArgMetAsnGlnSer
LeuSerLeuLeuTyrAsnValProAlaValAlaGluGluIleGlnAspGluValAspGluLeuLeuGlnLysGluGlnAsnTyrSerAsp
AspValLeuAlaAsnMetIleSerGluProArgIleSerTyrGlyAsnAspAlaLeuMetProSerLeuThrGluThrLysThrThrValGluLeu
LeuProValAsnGlyGluPheSerLeuAspAspLeuGlnProTrpHisSerPheGlyAlaAspSerValProAlaAsnThrGluAsn
GluValGluProValAspAlaArgProAlaAlaAspArgGlyLeuThrThrArgProGlySerGlyLeuThrAsnIleLysThrGluGluIleSer
GluValLysMetAspAlaGluPheArgHisAspSerGlyTyrGluValHisHisGlnLysLeuValPhePheAlaGluAspValGly
SerAsnLysGlyAlaIleIleGlyLeuMetValGlyGlyValValIleAlaThrValIleValIleThrLeuValMetLeuLysLysLysGlnTyrThr
SerIleHisHisGlyValValGluValAspAlaAlaVarThrProGluGluArgHisLeuSerLysMetGlnGlnAsnGlyTyrGluAsnProThr
TyrLysPhePheGluGlnMetGlnAsn

FIG. 3
(SEQ. ID NO. 3)

MetAlaAsnLeuGlyCysTrpMetLeuValLeuPheValAlaThrTrpSerAspLeuGlyLeuCysLysLysArgProLysProGlyGlyTrp
AsnThrGlyGlySerArgTyrProGlyGlnGlySerProGlyGlyAsnArgTyrProProGlnGlyGlyGlyGlyTrpGlyGlnPro
HisGlyGlyGlyTrpGlyGlnProHisGlyGlyGlyTrpGlyGlnProHisGlyGlyGlyTrpGlyGlnProHisGlyGlyGlyTrpGly
GlnGlyGlyGlyThrHisSerGlnTrpAsnLysProSerLysProLysThrAsnMetLysHisMetAlaGlyAlaAlaAlaAlaGlyAla
ValValGlyGlyLeuGlyGlyTyrMetLeuGlySerAlaMetSerArgProIleIleHisPheGlySerAspTyrGluAspArgTyrTyrArgGlu
AsnMetHisArgTyrProAsnGlnValTyrTyrArgProMetAspGluTyrSerAsnGlnAsnAsnPheValHisAspCysValAsnIleThrIl
eLysGlnHisThrValThrThrThrThrLysGlyGluAsnPheThrGluThrAspValLysMetMetGluArgValValGluGlnMetCysIleT
hrGlnTyrGluArgGluSerGlnAlaTyrTyrGlnArgGlySerSerMetValLeuPheSerSerProProValIleLeuLeu
IleSerPheLeuIlePheLeuIleValGly

FIG. 4
(SEQ. ID NO. 4)

MetAspValPheMetLysGlyLeuSerLysAlaLysGluGlyValValAlaAlaAlaGluLysThrLysGlnGlyValAlaGluAlaAla
GlyLysThrLysGluGlyValLeuTyrValGlySerLysThrLysGluGlyValValHisGlyValAlaThrValAlaGluLysThrLysGluGln
ValThrAsnValGlyGlyAlaValValThrGlyValThrAlaValAlaGlnLysThrValGluGlyAlaGlySerIleAlaAlaAlaThrThrGlyP
heValLysLysAspGlnLeuGlyLysAsnGluGluGlyAlaProGlnGluGlyIleLeuGluAspMetProValAspProAspAsnGluAlaTy
rGluMetProSerGluGluGlyTyrGlnAspTyrGluProGluAla

FIG. 5
(SEQ. ID NO. 5)

MetAlaGluProArgGlnGluPheGluValMetGluAspHisAlaGlyThrTyrGlyLeuGlyAspArgLysAspGlnGlyGlyTyrThrMet
HisGlnAspGlnGluGlyAspThrAspAlaGlyLeuLysGluSerProLeuGlnThrProThrGluAspGlySerGluGluProGly
SerGluThrSerAspAlaLysSerThrProThrAlaGluAspValThrAlaProLeuValAspGluGlyAlaProGlyLysGlnAlaAlaAlaGln
ProHisThrGluIleProGluGlyThrThrAlaGluGluAlaGlyIleGlyAspThrProSerLeuGluAspGluAlaAlaGlyHisVal
ThrGlnGluProGluSerGlyLysValValGlnGluGlyPheLeuArgGluProGlyProProGlyLeuSerHisGlnLeuMetSerGly
MetProGlyAlaProLeuLeuProGluGlyProArgGluAlaThrArgGlnProSerGlyThrGlyProGluAspThrGluGlyGlyArg
HisAlaProGluLeuLeuLysHisGlnLeuLeuGlyAspLeuHisGlnGlyProProLeuLysGlyAlaGlyGlyLysGluArgPro
GlySerLysGluValAspGluAspArgAspValAspGluSerSerProGlnAspSerProProSerLysAlaSerProAlaGlnAsp
GlyArgProProGlnThrAlaAlaArgGluAlaThrSerIleProGlyPheProAlaGluGlyAlaIleProLeuProValAspPheLeuSer
LysValSerThrGluIleProAlaSerGluProAspGlyProSerValGlyArgAlaLysGlyGlnAspAlaProLeuGluPheThrPheHisVal
GluIleThrProAsnValGlnLysGluGlnAlaHisSerGluGluHisLeuGlyArgAlaAlaPheProGlyAlaProGlyGluGlyProGluAla
ArgGlyProSerLeuGlyGluAspThrLysGluAlaAspLeuProGluProSerGluLysGlnProAlaAlaAlaProArgGly
LysProValSerArgValProGlnLeuLysAlaArgMetValSerLysSerLysAspGlyThrGlySerAspAspLysLysAlaLysThr
SerThrArgSerSerAlaLysThrLeuLysAsnArgProCysLeuSerProLysLeuProThrProGlySerSerAspProLeuIleGlnPro
SerSerProAlaValCysProGluProProSerSerProLysHisValSerSerValThrSerArgThrGlySerSerGlyAlaLysGluMet
LysLeuLysGlyAlaAspGlyLysThrLysIleAlaThrProArgGlyAlaAlaProProGlyGlnLysGlyGlnAlaAsnAlaThrArgIlePro
AlaLysThrProProAlaProLysThrProProSerSerGlyGluProProLysSerGlyAspArgSerGlyTyrSerSerProGlySer
ProGlyThrProGlySerArgSerArgThrProSerLeuProThrProProThrArgGluProLysLysValAlaValValArgThrProProLysS
erProSerSerAlaLysSerArgLeuGlnThrAlaProValProMetProAspLeuLysAsnValLysSerLysIleGlySerThrGluAsnLeuLy
sHisGlnProGlyGlyGlyLysValGlnIleIleAsnLysLysLeuAspLeuSerAsnValGlnSerLysCysGlySerLysAspAsnIleLysHis
ValProGlyGlyGlySerValGlnIleValTyrLysProValAspLeuSerLysValThrSerLysCysGlySerLeuGly
AsnIleHisHisLysProGlyGlyGlyGlnValGluValLysSerGluLysLeuAspPheLysAspArgValGlnSerLysIleGlySerLeuAsp
AsnIleThrHisValProGlyGlyGlyAsnLysLysIleGluThrHisLysLeuThrPheArgGluAsnAlaLysAlaLysThrAspHisGlyAla
GluIleValTyrLysSerProValValSerGlyAspThrSerProArgHisLeuSerAsnValSerSerThrGlySerIleAspMet
ValAspSerProGlnLeuAlaThrLeuAlaAspGluValSerAlaSerLeuAlaLysGlnGlyLeu

FIG. 6
(SEQ. ID NO. 6)

MetAlaThrLysAlaValCysValLeuLysGlyAspGlyProValGlnGlyIleIleAsnPheGluGlnLysGluSerAsnGlyProValLysVal
TrpGlySerIleLysGlyLeuThrGluGlyLeuHisGlyPheHisValHisGluPheGlyAspAsnThrAlaGlyCysThrSerAlaGlyProHis
PheAsnProLeuSerArgLysHisGlyGlyProLysAspGluGluArgHisValGlyAspLeuGlyAsnValThrAlaAspLys
AspGlyValAlaAspValSerIleGluAspSerValIleSerLeuSerGlyAspHisCysIleIleGlyArgThrLeuValValHisGluLys
AlaAspAspLeuGlyLysGlyGlyAsnGluGluSerThrLysThrGlyAsnAlaGlySerArgLeuAlaCysGlyValIleGlyIleAlaGln

FIG. 7
(SEQ. ID NO. 7)

MetAlaThrLeuGluLysLeuMetLysAlaPheGluSerLeuLysSerPheGlnGlnGlnGlnGlnGlnGlnGlnGlnGlnGlnGlnGlnGlnGlnGlnGlnGlnGlnGlnProProProProProProProProProProProGlnLeuProGlnProProProGlnAlaGlnProLeuProGlnProGlnProProProProProProProProProProGlyProAlaValAlaGluGluProLeuHisArgProLysLysGluLeuSerAlaThrLysLysAsp ArgValAsnHisCysLeuThrIleCysGluAsnIleValAlaGlnSerValArgAsnSerProGluPheGlnLysLeuLeuGlyIleAlaMetGlu LeuPheLeuLeuCysSerAspAspAlaGluSerAspValArgMetValAlaAspGluCysLeuAsnLysValIle LysAlaLeuMetAspSerAsnLeuProArgLeuGlnLeuGluLeuTyrLysGluIleLysLysAsnGlyAlaProArgSerLeuArgAla AlaLeuTrpArgPheAlaGluLeuAlaHisLeuValArgProGlnLysCysArgProTyrLeuValAsnLeuLeuProCysLeuThrArgThrS erLysArgProGluGluSerValGlnGluThrLeuAlaAlaAlaValProLysIleMetAlaSerPheGlyAsnPheAlaAsnAsp AsnGluIleLysValLeuLeuLysAlaPheIleAlaAsnLeuLysSerSerProThrIleArgArgThrAlaAlaGlySerAlaValSerIleCys GlnHisSerArgArgThrGlnTyrPheTyrSerTrpLeuLeuAsnValLeuLeuGlyLeuLeuValProValGluAspGluHisSer ThrLeuLeuIleLeuGlyValLeuLeuThrLeuArgTyrLeuValProLeuLeuGlnGlnGlnValLysAspThrSerLeuLysGlySer PheGlyValThrArgLysGluMetGluValSerProSerAlaGluGlnLeuValGlnValTyrGluLeuThrLeuHisHisThrGlnHis GlnAspHisAsnValValThrGlyAlaLeuGluLeuLeuGlnGlnLeuPheArgThrProProProGluLeuLeuGlnThrLeuThrAlaValG lyGlyIleGlyGlnLeuThrAlaAlaLysGluGluSerGlyGlyArgSerArgSerGlySerIleValGluLeuIleAlaGlyGlyGly SerSerCysSerProValLeuSerArgLysGlnLysGlyLysValLeuLeuGlyGluGluGluAlaLeuGluAspAspSerGluSerArg SerAspValSerSerSerAlaLeuThrAlaSerValLysAspGluIleSerGlyGluLeuAlaAlaSerSerGlyValSerThrProGlySer AlaGlyHisAspIleIleThrGluGlnProArgSerGlnHisThrLeuGlnAlaAspSerValAspLeuAlaSerCysAspLeuThrSerSerAlaT hrAspGlyAspGluGluAspIleLeuSerHisSerSerSerGlnValSerAlaValProSerAspProAlaMetAspLeuAsnAspGlyThrGlnA laSerSerProIleSerAspSerSerGlnThrThrThrGluGlyProAspSerAlaVarThrProSerAspSerSerGluIleValLeuAspGlyThrA spAsnGlnTyrLeuGlyLeuGlnIleGlyGlnProGlnAspGluAspGluGluAlaThrGlyIleLeuProAspGluAla SerGluAlaPheArgAsnSerSerMetAlaLeuGlnGlnAlaHisLeuLeuLysAsnMetSerHisCysArgGlnProSerAspSerSer ValAspLysPheValLeuArgAspGluAlaThrGluProGlyAspGlnGluAsnLysProCysArgIleLysGlyAspIleGlyGlnSer ThrAspAspAspSerAlaProLeuValHisCysValArgLeuLeuSerAlaSerPheLeuLeuThrGlyGlyLysAsnValLeuValPro AspArgAspValArgValSerValLysAlaLeuAlaLeuSerCysValGlyAlaAlaValAlaLeuHisProGluSerPhePheSerLys LeuTyrLysValProLeuAspThrThrGluTyrProGluGluGlnTyrValSerAspIleLeuAsnTyrIleAspHisGlyAspProGlnValArg GlyAlaThrAlaIleLeuCysGlyThrLeuIleCysSerIleLeuSerArgSerArgPheHisValGlyAspTrpMetGlyThrIleArg ThrLeuThrGlyAsnThrPheSerLeuAlaAspCysIleProLeuLeuArgLysThrLeuLysAspGluSerSerValThrCysLysLeu AlaCysThrAlaValArgAsnCysValMetSerLeuCysSerSerSerTyrSerGluLeuGlyLeuGlnLeuIleIleAspValLeuThrLeuArg AsnSerSerTyrTrpLeuValArgThrGluLeuLeuGluThrLeuAlaGluIleAspPheArgLeuValSerPheLeuGluAlaLys AlaGluAsnLeuHisArgGlyAlaHisHisTyrThrGlyLeuLeuLysLeuGlnGluArgValLeuAsnAsnValValIleHisLeuLeu GlyAspGluAspProArgValArgHisValAlaAlaAlaSerLeuIleArgLeuValProLysLeuPheTyrLysCysAspGlnGlyGln AlaAspProValValAlaValAlaArgAspGlnSerSerValTyrLeuLysLeuLeuMetHisGluThrGlnProProSerHisPheSerValSer ThrIleThrArgIleTyrArgGlyTyrAsnLeuLeuProSerIleThrAspValThrMetGluAsnAsnLeuSerArgValIleAlaAla ValSerHisGluLeuIleThrSerThrThrArgAlaLeuThrPheGlyCysCysGluAlaLeuCysLeuLeuSerThrAlaPheProValCysIleT rpSerLeuGlyTrpHisCysGlyValProProLeuSerAlaSerAspGluSerArgLysSerCysThrValGlyMetAlaThrMetIle LeuThrLeuLeuSerSerAlaTrpPheProLeuAspLeuSerAlaHisGlnAspAlaLeuIleLeuAlaGlyAsnLeuLeuAlaAlaSerAlaPro LysSerLeuArgSerSerTrpAlaSerGluGluGluAlaAsnProAlaAlaThrLysGlnGluGluValTrpProAlaLeuGlyAsp ArgAlaLeuValProMetValGluGlnLeuPheSerHisLeuLeuLysValIleAsnIleCysAlaHisValLeuAspAspValAlaProGlyPro AlaIleLysAlaAlaLeuProSerLeuThrAsnProProSerLeuSerProIleArgArgLysGlyLysGluLysGluProGlyGluGln AlaSerValProLeuSerProLysLysGlySerGluAlaSerAlaAlaSerArgGlnSerAspThrSerGlyProValThrThrSerLysSer SerSerLeuGlySerPheTyrHisLeuProSerTyrLeuLysLeuHisAspValLeuLysAlaThrHisAlaAsnTyrLysValThrLeu AspLeuGlnAsnSerThrGluLysPheGlyGlyPheLeuArgSerAlaLeuAspValLeuSerGlnIleLeuGluLeuAlaThrLeuGln AspIleGlyLysCysValGluGluIleLeuGlyTyrLeuLysSerCysPheSerArgGluProMetMetAlaThrValCysValGlnGln LeuLeuLysThrLeuPheGlyThrAsnLeuAlaSerGlnPheAspGlyLeuSerSerAsnProSerLysSerGlnGlyArgAlaGlnArg LeuGlySerSerSerValArgProGlyLeuTyrHisTyrCysPheMetAlaProTyrThrHisPheThrGlnAlaLeuAlaAspAlaSerLeuArg AsnMetValGlnAlaGluGlnGluAsnAspThrSerGlyTrpPheAspValLeuGlnLysValSerThrGlnLeuLysThrAsnLeuThrSerV alThrLysAsnArgAlaAspLysAsnAlaIleHisAsnHisIleArgLeuPheGluProLeuValIleLysAlaLeuLysGlnTyrThrThrThrTh rCysValGlnLeuGlnLysGlnValLeuAspLeuLeuAlaGlnLeuValGlnLeuArgValAsnTyrCysLeuLeuAspSerAspGlnValPh eIleGlyPheValLeuLysGlnPheGluTyrIleGluValGlyGlnPheArgGluSerGluAlaIleIleProAsnIlePhePhePheLeuValLeuLe uSerTyrGluArgTyrHisSerLysGlnIleIleGlyIleProLysIleIleGlnLeuCysAspGlyIleMetAlaSerGlyArgLysAlaSerProGlnP roTyrArgLeuCysSerPro

SEQUENCE LISTING

```
<160> NUMBER OF SEQ ID NOS: 7

<210> SEQ ID NO 1
<211> LENGTH: 43
<212> TYPE: PRT
<213> ORGANISM: homo sapiens
<300> PUBLICATION INFORMATION:
<308> DATABASE ACCESSION NUMBER: NCBI ENTREZ / QRHUA4
<309> DATABASE ENTRY DATE: 2000-09-15
<313> RELEVANT RESIDUES: (672)..(714)

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 2
<211> LENGTH: 770
<212> TYPE: PRT
<213> ORGANISM: homo sapiens
<300> PUBLICATION INFORMATION:
<308> DATABASE ACCESSION NUMBER: NCBI ENTREZ / QRHUA4
<309> DATABASE ENTRY DATE: 2000-09-15
<313> RELEVANT RESIDUES: (1)..(770)

<400> SEQUENCE: 2

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45
```

-continued

```
Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
            355                 360                 365

Ala Ser Thr Pro Asp Ala Val Asp Lys Tyr Leu Glu Thr Pro Gly Asp
            370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
            405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
            450                 455                 460

Leu Asn Asp Arg Arg Arg Leu Ala Leu Glu Asn Tyr Ile Thr Ala Leu
```

```
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
                500                 505                 510

Glu His Val Arg Met Val Asp Pro Lys Lys Ala Ala Gln Ile Arg Ser
                515                 520                 525

Gln Val Met Thr His Leu Arg Val Ile Tyr Glu Arg Met Asn Gln Ser
            530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
                595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
                675                 680                 685

Val Phe Phe Ala Glu Asp Val Gly Ser Asn Lys Gly Ala Ile Ile Gly
            690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
    770

<210> SEQ ID NO 3
<211> LENGTH: 253
<212> TYPE: PRT
<213> ORGANISM: homo sapiens
<300> PUBLICATION INFORMATION:
<308> DATABASE ACCESSION NUMBER: NCBI ENTREZ / XM_009567
<309> DATABASE ENTRY DATE: 2001-04-17
<313> RELEVANT RESIDUES: (1)..(253)

<400> SEQUENCE: 3

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45
```

```
Tyr Pro Pro Gln Gly Gly Gly Trp Gly Gln Pro His Gly Gly
    50                  55                  60

Trp Gly Gln Pro His Gly Gly Trp Gly Gln Pro His Gly Gly Gly
65                  70                  75                  80

Trp Gly Gln Pro His Gly Gly Trp Gly Gln Gly Gly Gly Thr His
                    85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Leu Gly Gly Tyr
            115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
                180                 185                 190

Thr Lys Gly Glu Asn Phe Thr Glu Thr Asp Val Lys Met Met Glu Arg
            195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

<210> SEQ ID NO 4
<211> LENGTH: 140
<212> TYPE: PRT
<213> ORGANISM: homo sapiens
<300> PUBLICATION INFORMATION:
<308> DATABASE ACCESSION NUMBER: NCBI ENTREZ / XM_003494
<309> DATABASE ENTRY DATE: 2001-04-16
<313> RELEVANT RESIDUES: (1)..(140)

<400> SEQUENCE: 4

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
        130                 135                 140
```

<210> SEQ ID NO 5
<211> LENGTH: 758
<212> TYPE: PRT
<213> ORGANISM: homo sapiens
<300> PUBLICATION INFORMATION:
<308> DATABASE ACCESSION NUMBER: NCBI ENTREZ / NM_016835
<309> DATABASE ENTRY DATE: 2001-02-13
<313> RELEVANT RESIDUES: (1)..(758)

<400> SEQUENCE: 5

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
```

-continued

```
                355                 360                 365
Ser Arg Val Pro Gln Leu Lys Ala Arg Met Val Ser Lys Ser Lys Asp
370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys Leu Pro Thr
                405                 410                 415
Pro Gly Ser Ser Asp Pro Leu Ile Gln Pro Ser Ser Pro Ala Val Cys
            420                 425                 430
Pro Glu Pro Pro Ser Ser Pro Lys His Val Ser Ser Val Thr Ser Arg
            435                 440                 445
Thr Gly Ser Ser Gly Ala Lys Glu Met Lys Leu Lys Gly Ala Asp Gly
450                 455                 460
Lys Thr Lys Ile Ala Thr Pro Arg Gly Ala Ala Pro Pro Gly Gln Lys
465                 470                 475                 480
Gly Gln Ala Asn Ala Thr Arg Ile Pro Ala Lys Thr Pro Pro Ala Pro
                485                 490                 495
Lys Thr Pro Pro Ser Ser Gly Glu Pro Lys Ser Gly Asp Arg Ser
            500                 505                 510
Gly Tyr Ser Ser Pro Gly Ser Pro Gly Thr Pro Gly Ser Arg Ser Arg
            515                 520                 525
Thr Pro Ser Leu Pro Thr Pro Thr Arg Glu Pro Lys Lys Val Ala
            530                 535                 540
Val Val Arg Thr Pro Pro Lys Ser Pro Ser Ser Ala Lys Ser Arg Leu
545                 550                 555                 560
Gln Thr Ala Pro Val Pro Met Pro Asp Leu Lys Asn Val Lys Ser Lys
                565                 570                 575
Ile Gly Ser Thr Glu Asn Leu Lys His Gln Pro Gly Gly Gly Lys Val
                580                 585                 590
Gln Ile Ile Asn Lys Lys Leu Asp Leu Ser Asn Val Gln Ser Lys Cys
            595                 600                 605
Gly Ser Lys Asp Asn Ile Lys His Val Pro Gly Gly Gly Ser Val Gln
            610                 615                 620
Ile Val Tyr Lys Pro Val Asp Leu Ser Lys Val Thr Ser Lys Cys Gly
625                 630                 635                 640
Ser Leu Gly Asn Ile His His Lys Pro Gly Gly Gln Val Glu Val
                645                 650                 655
Lys Ser Glu Lys Leu Asp Phe Lys Asp Arg Val Gln Ser Lys Ile Gly
            660                 665                 670
Ser Leu Asp Asn Ile Thr His Val Pro Gly Gly Asn Lys Lys Ile
            675                 680                 685
Glu Thr His Lys Leu Thr Phe Arg Glu Asn Ala Lys Ala Lys Thr Asp
690                 695                 700
His Gly Ala Glu Ile Val Tyr Lys Ser Pro Val Val Ser Gly Asp Thr
705                 710                 715                 720
Ser Pro Arg His Leu Ser Asn Val Ser Ser Thr Gly Ser Ile Asp Met
                725                 730                 735
Val Asp Ser Pro Gln Leu Ala Thr Leu Ala Asp Glu Val Ser Ala Ser
            740                 745                 750
Leu Ala Lys Gln Gly Leu
            755
```

<210> SEQ ID NO 6

```
<211> LENGTH: 154
<212> TYPE: PRT
<213> ORGANISM: homo sapiens
<300> PUBLICATION INFORMATION:
<308> DATABASE ACCESSION NUMBER: NCBI ENTREZ / P00441
<309> DATABASE ENTRY DATE: 2000-05-30
<313> RELEVANT RESIDUES: (1)..(154)

<400> SEQUENCE: 6
```

| Met | Ala | Thr | Lys | Ala | Val | Cys | Val | Leu | Lys | Gly | Asp | Gly | Pro | Val | Gln |
|---|---|---|---|---|---|---|---|---|---|---|---|---|---|---|---|
| 1 | | | | 5 | | | | | 10 | | | | | 15 | |

| Gly | Ile | Ile | Asn | Phe | Glu | Gln | Lys | Glu | Ser | Asn | Gly | Pro | Val | Lys | Val |
|---|---|---|---|---|---|---|---|---|---|---|---|---|---|---|---|
| | | | 20 | | | | | 25 | | | | | 30 | | |

| Trp | Gly | Ser | Ile | Lys | Gly | Leu | Thr | Glu | Gly | Leu | His | Gly | Phe | His | Val |
|---|---|---|---|---|---|---|---|---|---|---|---|---|---|---|---|
| | | 35 | | | | | 40 | | | | | 45 | | | |

| His | Glu | Phe | Gly | Asp | Asn | Thr | Ala | Gly | Cys | Thr | Ser | Ala | Gly | Pro | His |
|---|---|---|---|---|---|---|---|---|---|---|---|---|---|---|---|
| | 50 | | | | | 55 | | | | | 60 | | | | |

| Phe | Asn | Pro | Leu | Ser | Arg | Lys | His | Gly | Gly | Pro | Lys | Asp | Glu | Glu | Arg |
|---|---|---|---|---|---|---|---|---|---|---|---|---|---|---|---|
| 65 | | | | | 70 | | | | | 75 | | | | | 80 |

| His | Val | Gly | Asp | Leu | Gly | Asn | Val | Thr | Ala | Asp | Lys | Asp | Gly | Val | Ala |
|---|---|---|---|---|---|---|---|---|---|---|---|---|---|---|---|
| | | | | 85 | | | | | 90 | | | | | 95 | |

| Asp | Val | Ser | Ile | Glu | Asp | Ser | Val | Ile | Ser | Leu | Ser | Gly | Asp | His | Cys |
|---|---|---|---|---|---|---|---|---|---|---|---|---|---|---|---|
| | | | | 100 | | | | | 105 | | | | | 110 | |

| Ile | Ile | Gly | Arg | Thr | Leu | Val | Val | His | Glu | Lys | Ala | Asp | Asp | Leu | Gly |
|---|---|---|---|---|---|---|---|---|---|---|---|---|---|---|---|
| | | | 115 | | | | | 120 | | | | | 125 | | |

| Lys | Gly | Gly | Asn | Glu | Glu | Ser | Thr | Lys | Thr | Gly | Asn | Ala | Gly | Ser | Arg |
|---|---|---|---|---|---|---|---|---|---|---|---|---|---|---|---|
| | 130 | | | | | 135 | | | | | 140 | | | | |

| Leu | Ala | Cys | Gly | Val | Ile | Gly | Ile | Ala | Gln |
|---|---|---|---|---|---|---|---|---|---|
| 145 | | | | | 150 | | | | |

```
<210> SEQ ID NO 7
<211> LENGTH: 1543
<212> TYPE: PRT
<213> ORGANISM: homo sapiens
<300> PUBLICATION INFORMATION:
<308> DATABASE ACCESSION NUMBER: NCBI ENTREZ / XP_003405
<309> DATABASE ENTRY DATE: 2001-04-16
<313> RELEVANT RESIDUES: (1)..(1543)

<400> SEQUENCE: 7
```

| Met | Ala | Thr | Leu | Glu | Lys | Leu | Met | Lys | Ala | Phe | Glu | Ser | Leu | Lys | Ser |
|---|---|---|---|---|---|---|---|---|---|---|---|---|---|---|---|
| 1 | | | | 5 | | | | | 10 | | | | | 15 | |

| Phe | Gln | Gln | Gln | Gln | Gln | Gln | Gln | Gln | Gln | Gln | Gln | Gln | Gln | Gln | Gln |
|---|---|---|---|---|---|---|---|---|---|---|---|---|---|---|---|
| | | | 20 | | | | | 25 | | | | | 30 | | |

| Gln | Gln | Gln | Gln | Gln | Pro | Pro | Pro | Pro | Pro | Pro | Pro | Pro | Pro | Pro | Pro |
|---|---|---|---|---|---|---|---|---|---|---|---|---|---|---|---|
| | | 35 | | | | | 40 | | | | | 45 | | | |

| Gln | Leu | Pro | Gln | Pro | Pro | Pro | Gln | Ala | Gln | Pro | Leu | Leu | Pro | Gln | Pro |
|---|---|---|---|---|---|---|---|---|---|---|---|---|---|---|---|
| | 50 | | | | | 55 | | | | | 60 | | | | |

| Gln | Pro | Pro | Pro | Pro | Pro | Pro | Pro | Pro | Gly | Pro | Ala | Val | Ala |
|---|---|---|---|---|---|---|---|---|---|---|---|---|---|
| 65 | | | | | 70 | | | | | 75 | | | | 80 |

| Glu | Glu | Pro | Leu | His | Arg | Pro | Lys | Lys | Glu | Leu | Ser | Ala | Thr | Lys | Lys |
|---|---|---|---|---|---|---|---|---|---|---|---|---|---|---|---|
| | | | | 85 | | | | | 90 | | | | | 95 | |

| Asp | Arg | Val | Asn | His | Cys | Leu | Thr | Ile | Cys | Glu | Asn | Ile | Val | Ala | Gln |
|---|---|---|---|---|---|---|---|---|---|---|---|---|---|---|---|
| | | | | 100 | | | | | 105 | | | | | 110 | |

| Ser | Val | Arg | Asn | Ser | Pro | Glu | Phe | Gln | Lys | Leu | Leu | Gly | Ile | Ala | Met |
|---|---|---|---|---|---|---|---|---|---|---|---|---|---|---|---|
| | | | 115 | | | | | 120 | | | | | 125 | | |

| Glu | Leu | Phe | Leu | Leu | Cys | Ser | Asp | Asp | Ala | Glu | Ser | Asp | Val | Arg | Met |
|---|---|---|---|---|---|---|---|---|---|---|---|---|---|---|---|
| | 130 | | | | | 135 | | | | | 140 | | | | |

-continued

```
Val Ala Asp Glu Cys Leu Asn Lys Val Ile Lys Ala Leu Met Asp Ser
145                 150                 155                 160

Asn Leu Pro Arg Leu Gln Leu Glu Leu Tyr Lys Glu Ile Lys Lys Asn
            165                 170                 175

Gly Ala Pro Arg Ser Leu Arg Ala Ala Leu Trp Arg Phe Ala Glu Leu
                180                 185                 190

Ala His Leu Val Arg Pro Gln Lys Cys Arg Pro Tyr Leu Val Asn Leu
        195                 200                 205

Leu Pro Cys Leu Thr Arg Thr Ser Lys Arg Pro Glu Glu Ser Val Gln
    210                 215                 220

Glu Thr Leu Ala Ala Val Pro Lys Ile Met Ala Ser Phe Gly Asn
225                 230                 235                 240

Phe Ala Asn Asp Asn Glu Ile Lys Val Leu Lys Ala Phe Ile Ala
                245                 250                 255

Asn Leu Lys Ser Ser Ser Pro Thr Ile Arg Arg Thr Ala Ala Gly Ser
            260                 265                 270

Ala Val Ser Ile Cys Gln His Ser Arg Arg Thr Gln Tyr Phe Tyr Ser
        275                 280                 285

Trp Leu Leu Asn Val Leu Leu Gly Leu Leu Val Pro Val Glu Asp Glu
    290                 295                 300

His Ser Thr Leu Leu Ile Leu Gly Val Leu Leu Thr Leu Arg Tyr Leu
305                 310                 315                 320

Val Pro Leu Leu Gln Gln Gln Val Lys Asp Thr Ser Leu Lys Gly Ser
                325                 330                 335

Phe Gly Val Thr Arg Lys Glu Met Glu Val Ser Pro Ser Ala Glu Gln
                340                 345                 350

Leu Val Gln Val Tyr Glu Leu Thr Leu His His Thr Gln His Gln Asp
            355                 360                 365

His Asn Val Val Thr Gly Ala Leu Glu Leu Leu Gln Gln Leu Phe Arg
        370                 375                 380

Thr Pro Pro Pro Glu Leu Leu Gln Thr Leu Thr Ala Val Gly Gly Ile
385                 390                 395                 400

Gly Gln Leu Thr Ala Ala Lys Glu Glu Ser Gly Gly Arg Ser Arg Ser
                405                 410                 415

Gly Ser Ile Val Glu Leu Ile Ala Gly Gly Ser Ser Cys Ser Pro
                420                 425                 430

Val Leu Ser Arg Lys Gln Lys Gly Lys Val Leu Leu Gly Glu Glu Glu
            435                 440                 445

Ala Leu Glu Asp Asp Ser Glu Ser Arg Ser Asp Val Ser Ser Ser Ala
450                 455                 460

Leu Thr Ala Ser Val Lys Asp Glu Ile Ser Gly Glu Leu Ala Ala Ser
465                 470                 475                 480

Ser Gly Val Ser Thr Pro Gly Ser Ala Gly His Asp Ile Ile Thr Glu
                485                 490                 495

Gln Pro Arg Ser Gln His Thr Leu Gln Ala Asp Ser Val Asp Leu Ala
            500                 505                 510

Ser Cys Asp Leu Thr Ser Ser Ala Thr Asp Gly Asp Glu Glu Asp Ile
        515                 520                 525

Leu Ser His Ser Ser Ser Gln Val Ser Ala Val Pro Ser Asp Pro Ala
    530                 535                 540

Met Asp Leu Asn Asp Gly Thr Gln Ala Ser Ser Pro Ile Ser Asp Ser
545                 550                 555                 560

Ser Gln Thr Thr Thr Glu Gly Pro Asp Ser Ala Val Thr Pro Ser Asp
```

-continued

```
                565                 570                 575
Ser Ser Glu Ile Val Leu Asp Gly Thr Asp Asn Gln Tyr Leu Gly Leu
            580                 585                 590
Gln Ile Gly Gln Pro Gln Asp Glu Asp Glu Ala Thr Gly Ile Leu
            595                 600                 605
Pro Asp Glu Ala Ser Glu Ala Phe Arg Asn Ser Ser Met Ala Leu Gln
            610                 615                 620
Gln Ala His Leu Leu Lys Asn Met Ser His Cys Arg Gln Pro Ser Asp
625                 630                 635                 640
Ser Ser Val Asp Lys Phe Val Leu Arg Asp Glu Ala Thr Glu Pro Gly
                645                 650                 655
Asp Gln Glu Asn Lys Pro Cys Arg Ile Lys Gly Asp Ile Gly Gln Ser
            660                 665                 670
Thr Asp Asp Asp Ser Ala Pro Leu Val His Cys Val Arg Leu Leu Ser
            675                 680                 685
Ala Ser Phe Leu Leu Thr Gly Gly Lys Asn Val Leu Val Pro Asp Arg
690                 695                 700
Asp Val Arg Val Ser Val Lys Ala Leu Ala Leu Ser Cys Val Gly Ala
705                 710                 715                 720
Ala Val Ala Leu His Pro Glu Ser Phe Phe Ser Lys Leu Tyr Lys Val
                725                 730                 735
Pro Leu Asp Thr Thr Glu Tyr Pro Glu Glu Gln Tyr Val Ser Asp Ile
            740                 745                 750
Leu Asn Tyr Ile Asp His Gly Asp Pro Gln Val Arg Gly Ala Thr Ala
            755                 760                 765
Ile Leu Cys Gly Thr Leu Ile Cys Ser Ile Leu Ser Arg Ser Arg Phe
            770                 775                 780
His Val Gly Asp Trp Met Gly Thr Ile Arg Thr Leu Thr Gly Asn Thr
785                 790                 795                 800
Phe Ser Leu Ala Asp Cys Ile Pro Leu Leu Arg Lys Thr Leu Lys Asp
                805                 810                 815
Glu Ser Ser Val Thr Cys Lys Leu Ala Cys Thr Ala Val Arg Asn Cys
            820                 825                 830
Val Met Ser Leu Cys Ser Ser Ser Tyr Ser Glu Leu Gly Leu Gln Leu
            835                 840                 845
Ile Ile Asp Val Leu Thr Leu Arg Asn Ser Ser Tyr Trp Leu Val Arg
850                 855                 860
Thr Glu Leu Leu Glu Thr Leu Ala Glu Ile Asp Phe Arg Leu Val Ser
865                 870                 875                 880
Phe Leu Glu Ala Lys Ala Glu Asn Leu His Arg Gly Ala His His Tyr
                885                 890                 895
Thr Gly Leu Leu Lys Leu Gln Glu Arg Val Leu Asn Asn Val Val Ile
            900                 905                 910
His Leu Leu Gly Asp Glu Asp Pro Arg Val Arg His Val Ala Ala Ala
            915                 920                 925
Ser Leu Ile Arg Leu Val Pro Lys Leu Phe Tyr Lys Cys Asp Gln Gly
            930                 935                 940
Gln Ala Asp Pro Val Val Ala Val Ala Arg Asp Gln Ser Ser Val Tyr
945                 950                 955                 960
Leu Lys Leu Leu Met His Glu Thr Gln Pro Pro Ser His Phe Ser Val
                965                 970                 975
Ser Thr Ile Thr Arg Ile Tyr Arg Gly Tyr Asn Leu Leu Pro Ser Ile
            980                 985                 990
```

```
Thr Asp Val Thr Met Glu Asn Asn  Leu Ser Arg Val Ile  Ala Ala Val
        995               1000               1005

Ser His Glu Leu Ile Thr Ser  Thr Thr Arg Ala Leu  Thr Phe Gly
    1010              1015               1020

Cys Cys Glu Ala Leu Cys Leu  Leu Ser Thr Ala Phe  Pro Val Cys
    1025              1030               1035

Ile Trp Ser Leu Gly Trp His  Cys Gly Val Pro Pro  Leu Ser Ala
    1040              1045               1050

Ser Asp Glu Ser Arg Lys Ser  Cys Thr Val Gly Met  Ala Thr Met
    1055              1060               1065

Ile Leu Thr Leu Leu Ser Ser  Ala Trp Phe Pro Leu  Asp Leu Ser
    1070              1075               1080

Ala His Gln Asp Ala Leu Ile  Leu Ala Gly Asn Leu  Leu Ala Ala
    1085              1090               1095

Ser Ala Pro Lys Ser Leu Arg  Ser Ser Trp Ala Ser  Glu Glu Glu
    1100              1105               1110

Ala Asn Pro Ala Ala Thr Lys  Gln Glu Glu Val Trp  Pro Ala Leu
    1115              1120               1125

Gly Asp Arg Ala Leu Val Pro  Met Val Glu Gln Leu  Phe Ser His
    1130              1135               1140

Leu Leu Lys Val Ile Asn Ile  Cys Ala His Val Leu  Asp Asp Val
    1145              1150               1155

Ala Pro Gly Pro Ala Ile Lys  Ala Ala Leu Pro Ser  Leu Thr Asn
    1160              1165               1170

Pro Pro Ser Leu Ser Pro Ile  Arg Arg Lys Gly Lys  Glu Lys Glu
    1175              1180               1185

Pro Gly Glu Gln Ala Ser Val  Pro Leu Ser Pro Lys  Lys Gly Ser
    1190              1195               1200

Glu Ala Ser Ala Ala Ser Arg  Gln Ser Asp Thr Ser  Gly Pro Val
    1205              1210               1215

Thr Thr Ser Lys Ser Ser Ser  Leu Gly Ser Phe Tyr  His Leu Pro
    1220              1225               1230

Ser Tyr Leu Lys Leu His Asp  Val Leu Lys Ala Thr  His Ala Asn
    1235              1240               1245

Tyr Lys Val Thr Leu Asp Leu  Gln Asn Ser Thr Glu  Lys Phe Gly
    1250              1255               1260

Gly Phe Leu Arg Ser Ala Leu  Asp Val Leu Ser Gln  Ile Leu Glu
    1265              1270               1275

Leu Ala Thr Leu Gln Asp Ile  Gly Lys Cys Val Glu  Glu Ile Leu
    1280              1285               1290

Gly Tyr Leu Lys Ser Cys Phe  Ser Arg Glu Pro Met  Met Ala Thr
    1295              1300               1305

Val Cys Val Gln Gln Leu Leu  Lys Thr Leu Phe Gly  Thr Asn Leu
    1310              1315               1320

Ala Ser Gln Phe Asp Gly Leu  Ser Ser Asn Pro Ser  Lys Ser Gln
    1325              1330               1335

Gly Arg Ala Gln Arg Leu Gly  Ser Ser Ser Val Arg  Pro Gly Leu
    1340              1345               1350

Tyr His Tyr Cys Phe Met Ala  Pro Tyr Thr His Phe  Thr Gln Ala
    1355              1360               1365

Leu Ala Asp Ala Ser Leu Arg  Asn Met Val Gln Ala  Glu Gln Glu
    1370              1375               1380
```

```
                                     -continued

Asn Asp Thr Ser Gly Trp Phe Asp Val Leu Gln Lys Val Ser Thr
    1385                1390             1395

Gln Leu Lys Thr Asn Leu Thr Ser Val Thr Lys Asn Arg Ala Asp
    1400            1405             1410

Lys Asn Ala Ile His Asn His Ile Arg Leu Phe Glu Pro Leu Val
    1415            1420             1425

Ile Lys Ala Leu Lys Gln Tyr Thr Thr Thr Thr Cys Val Gln Leu
    1430            1435             1440

Gln Lys Gln Val Leu Asp Leu Leu Ala Gln Leu Val Gln Leu Arg
    1445            1450             1455

Val Asn Tyr Cys Leu Leu Asp Ser Asp Gln Val Phe Ile Gly Phe
    1460            1465             1470

Val Leu Lys Gln Phe Glu Tyr Ile Glu Val Gly Gln Phe Arg Glu
    1475            1480             1485

Ser Glu Ala Ile Ile Pro Asn Ile Phe Phe Phe Leu Val Leu Leu
    1490            1495             1500

Ser Tyr Glu Arg Tyr His Ser Lys Gln Ile Ile Gly Ile Pro Lys
    1505            1510             1515

Ile Ile Gln Leu Cys Asp Gly Ile Met Ala Ser Gly Arg Lys Ala
    1520            1525             1530

Ser Pro Gln Pro Tyr Arg Leu Cys Ser Pro
    1535            1540
```

METHODS AND COMPOSITIONS FOR CONTROLLING PROTEIN ASSEMBLY OR AGGREGATION

CROSS-REFERENCE TO RELATED APPLICATIONS

This is a continuation-in-part of U.S. patent application Ser. No. 09/677,500, filed Oct. 2, 2000 now U.S. Pat. No. 6,407,125, which is a continuation-in-part of U.S. patent application Ser. No. 09/657,554, filed Sep. 8, 2000 (now U.S. Pat. No. 6,579,891), a continuation-in-part of U.S. patent application Ser. No. 09/657,989, filed Sep. 8, 2000 (now U.S. Pat. No. 6,410,570), and a continuation-in-part of U.S. patent application Ser. No. 09/127,620, filed Aug. 1, 1998 (now U.S. Pat. No. 6,127,393), which is a continuation-in-part of U.S. patent application Ser. No. 08/843,157, filed Apr. 11, 1997, now abandoned, which is a continuation-in-part of U.S. patent application Ser. No. 08/581,351, filed Dec. 29, 1995 (now U.S. Pat. No. 5,767,135), which claims priority to U.S. Provisional Patent Application Ser. No. 60/024,221, filed Oct. 22, 1996 and to U.S. Provisional Patent Application Ser. No. 60/026,992, filed Sep. 20, 1996.

STATEMENT REGARDING FEDERALLY SPONSORED RESEARCH OR DEVELOPMENT

Not Applicable.

REFERENCE TO A MICROFICHE APPENDIX

Not Applicable.

FIELD OF THE INVENTION

This invention relates to compositions and methods for the treatment of degenerative diseases. More specifically, the invention relates to pharmaceutical compositions and methods for the treatment of degenerative diseases related to aggregation or assembly of conformationally altered proteins including, but not limited to Alzheimer's disease, cerebral amyloid angiopathy, Parkinson's disease, frontal temporal dementia, Pick's disease, amyotrophic lateral sclerosis, Huntington's disease, bovine spongiform encephalopathy and Creutzfeld-Jakob disease.

BACKGROUND OF THE INVENTION

Assembly or aggregation of conformationally altered proteins is thought to be a major cause of prepathological and pathological conditions including amyloidoses, prion diseases, and other common degenerative diseases. Conformational alterations from α-helical or random coil to β-sheet conformation are believed to be required for the conversion of normally soluble and functional proteins into insoluble and pathogenic states. Examples of such insoluble proteins include: Beta-Amyloid Precursor Protein (APP) and Beta-Amyloid (βA) in amyloid plaques of Alzheimer's Disease (AD), Familial AD (FAD) and cerebral amyloid angiopathy (CAA); α-synuclein deposits in Lewy bodies of Parkinson's disease; Tau in neurofibrillary tangles in frontal temporal dementia and Pick's disease; Superoxide Dismutase in amyotrophic lateral sclerosis; Huntingtin in Huntington's disease; and Prion Protein (PrP) in Creutzfelds-Jakob disease (CJD). These conformationally altered insoluble proteins are composed mostly of fibrils formed by the assembly or aggregation of β-sheet monomers. It is believed that abnormal binding of a metal ligand in the metal-binding sites of the normal, soluble proteins is a major factor in the pathogenesis and continued pathology of the resulting diseases. It has also been suggested that certain forms of these diseases may be inherited. However, no methods currently exist to definitively link these diseases to genetic inheritance.

Currently, there is no effective therapy for PrP infection. There are also no treatments currently available that target the conformational changes from α-helical or random coil to β-sheet conformation to treat cerebral amyloid angiopathy, Parkinson's disease, frontal temporal dementia, Pick's disease, amyotrophic lateral sclerosis, or Huntington's disease. AD therapeutic agents such as acetylcholinesterase (AChE) inhibitors that enhance cholinergic neurotransmission by hindering the breakdown of acetylcholine have been approved by the FDA. This approach, however, does not retard the progression of the underlying neurodegenerative disease.

Nonspecific chelation therapy has become increasingly promoted as a therapy for AD and other diseases manifested by the aggregation or assembly of conformationally altered proteins. However, the growing practice of intravenous infusions of well-known nonspecific chelators such as ethylene-diamine-tetraacetic acid (EDTA) can lead to systemic metal ion depletion, making its use less desirable.

Therefore, novel compositions and methods are needed to treat diseases caused by the prepathological and pathological assembly or aggregation of proteins causing amyloidoses, prion diseases and other degenerative diseases that inhibit or reverse the progression of the underlying neurodegenerative disease and do not result in metal ion depletion.

BRIEF SUMMARY OF THE INVENTION

In overcoming the above disadvantages, it is an object of the invention to produce compositions that may be used to successfully treat degenerative diseases.

Accordingly, and in one aspect of the invention, a composition capable of solubilizing a conformationally altered protein that includes a carboxylic acid anion of picolinic acid, analogs, or derivatives, thereof and a cation is provided, wherein the composition is not zinc picolinate, chromium picolinate, molybdenum picolinic, iron picolinic, manganese picolinate, copper picolinate, boron picolinate or vanadium picolinate.

In a second aspect of the invention, the above-described composition of the invention comprises picolinic acid, its analogs, or derivatives.

In a third aspect of the invention, the above-described composition of the invention comprises fusaric acid.

In a fourth aspect of the invention, a method of preventing or reversing conformationally altered protein assembly or aggregation in an animal is provided that includes introducing picolinic acid, its analogs, or derivatives to the conformationally altered protein.

In a fifth aspect of the invention, a method of preventing or reversing conformationally altered protein assembly or aggregation in an animal is provided that includes introducing fusaric acid to the conformationally altered protein.

In a sixth aspect of the invention, a method of treating conformationally altered protein assembly or aggregation in an animal is provided that includes administering a therapeutically effective amount of the above-described compositions of the invention.

These and other objects, advantages and features of the invention will become apparent to those persons skilled in the art upon reading the details of the compounds and methods more fully described below.

BRIEF DESCRIPTION OF THE SEVERAL VIEWS OF THE DRAWINGS

FIG. 1 illustrates SEQ ID NO: 1, the polypeptide sequence of Beta-Amyloid (βA) as contained in Homo sapiens Beta-Amyloid Precursor Protein ($APP_{770}$) in GenBank Accession No. QRHUA4 from positions 672 to 714.

FIG. 2 illustrates SEQ ID NO 2, the entire polypeptide sequence of $APP_{770}$ in Homo sapiens.

FIG. 3 illustrates SEQ ID NO 3, the polypeptide sequence of Prion Protein in Homo sapiens.

FIG. 4 illustrates SEQ ID NO 4, the polypeptide sequence of α-Synuclein in Homo sapiens.

FIG. 5 illustrates SEQ ID NO 5, the polypeptide sequence of Tau in Homo sapiens.

FIG. 6 illustrates SEQ ID NO 6, the polypeptide sequence of Superoxide Dismutase in homo sapiens.

FIG. 7 illustrates SEQ ID NO 7, the polypeptide sequence of Huntingtin in Homo sapiens.

DETAILED DESCRIPTION OF THE INVENTION

Figure 8:
FIG. 8 illustrates the first forty amino acids of $βA_{1-40}$ incubated in the presence of Zn at a magnification of 1:52,000.

It has been discovered that conditions, diseases and disorders related to prepathological and pathological protein assembly or aggregation caused by conformational changes of proteins from α-helical or random coil to β-sheet conformation may be treated with compositions that are capable of solubilizing conformationally altered proteins. The compositions of the invention, capable of solubilizing conformationally altered proteins, comprise a carboxylic acid anion of picolinic acid, its analogs, or derivatives and a cation. Picolinic acid, also known as α-pyridine carboxylic acid and 2-pyridine carboxylic acid, is a naturally occurring biological metabolite known to inhibit the growth of numerous cultured normal and transformed mammalian cells. Picolinic acid has the formula $C_6H_5NO_2$, a molecular weight of 123.11 g/mol and is readily soluble in water.

The compositions of the invention do not include zinc picolinate, chromium picolinate, molybdenum picolinate, iron picolinate, manganese picolinate, copper picolinate, boron picolinate or vanadium picolinate. In one embodiment of the invention, the carboxylic acid anion of picolinic acid, its derivatives, or analogs thereof is represented by the following structure:

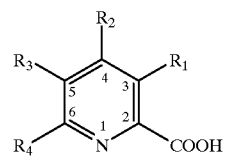

wherein $R_1$, $R_2$, $R_3$ and $R_4$ are selected from the group consisting of an oligopeptide, carboxyl group, methyl group, ethyl group, propyl group, isopropyl group, butyl group, isobutyl group, secondary butyl group, tertiary butyl group, pentyl group, isopentyl group, neopentyl group, fluorine, chlorine, bromine, iodine and hydrogen.

In one embodiment, groups $R_1$, $R_2$ and $R_4$ are hydrogen and group $R_3$ is a butyl group. Fusaric acid, the 5-butyl derivative of picolinic acid, wherein $R_1$, $R_2$ and $R_4$ are hydrogen and $R_3$ is a butyl group, was first isolated from the fungus *Fusarium heterosporium* in 1934. Fusaric acid has the chemical name 5-butyl-2-pyndinecarboxylic acid, or 5-butylpicolinic acid, has a chemical formula of $C_{10}H_{13}NO_2$, a molecular weight of 179.22, and is readily soluble in water. The compositions described herein are readily commercially available, or may be made by methods well known in the art.

The oligopeptide may be in the range of about 10–24 amino acids, preferably in the range of about 14–20 amino acids, and more preferably, 16 amino acids. It will be appreciated that substitutions at the $R_1$, $R_2$, $R_3$ and $R_4$ positions are made with an oligopeptide having basic or acidic amino acids predominating. Such substituted analogs or derivatives have an increased molecular weight and a substantially increased half-life in the blood. Such compounds are also able to penetrate cells more effectively both in vitro and in vivo due to the amphipathic nature of the peptide residues. See, e.g., U.S. Pat. No. 6,127,393, hereby incorporated by reference in its entirety.

Pharmaceutically acceptable salts of picolinic acid and the above analogs may also be prepared from pharmaceutically acceptable non-toxic acids or bases including, but not limited to inorganic and organic acids. Buffering agents for picolinic acid or its analogs or derivatives may also comprise non-toxic acids or bases including, but not limited to inorganic or organic acids. Examples of such inorganic acids include, but are not limited to hydrochloric, hydrobromic, hydroiodic, sulfuric and phosphoric. Organic acids may be selected, for example, from aliphatic, aromatic, carboxylic and sulfonic classes of organic acids. Examples of suitable organic acids include, but are not limited to formic, acetic, propionic, succinic, glycolic, glucoronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic and galacturonic acids. Examples of such inorganic bases for potential salt formation with the sulfate or phosphate compounds of the invention include, but are not limited to monovalent, divalent, or other metallic salts made from aluminum, calcium, lithium, magnesium, potassium, sodium and zinc. Appropriate organic bases may also be selected from N,N-dibenzylethylenediamine, chloroprocaine, choline, diethanolamine, ethylenediamine, meglumaine (N-methylglucamine), procaine, ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane and tetramethylammonium hydroxide.

The compositions of the invention also include a cation. Suitable cations include, but are not limited to aluminum, calcium, lithium, magnesium, potassium, sodium, ammonia, ethylenediamine, N-methyl-glutamine, lysine, arginine, omithine, choline, N, N'-dibenzyl ethylenediamine, chloroprocaine, diethanolamine, procaine, N-benzylphenethymine, diethylamine, piperazine, tris(hydroxyethyl) aminomethane and tetramethylammonium hydroxide cations.

In one embodiment, the compositions of the invention include at least one buffering agent. Any buffering agent may be used. Suitable buffering agents include, but are not limited to hydrochloric, hydrobromic, hydroiodic, sulfuric, phosphoric, formic, acetic, propionic, succinic, glycolic, glucoronic, maleic, furoic, citric, glutamic, benzoic, anthranilic, salicylic, phenylacetic, mandelic, embonic, pamoic, methanesulfonic, ethanesulfonic, pantothenic, benzenesulfonic, stearic, sulfanilic, algenic, galacturonic acid and mixtures thereof. The buffering agents may comprise one or more additional agents including, but not limited to pregelatinized maize starch, polyvinyl pyrrolidone, hydroxypropyl methylcellulose, lactose, microcrystalline cellulose, calcium hydrogen phosphate, magnesium stearate, talc, silica, potato starch, sodium starch glycolate, sodium lauryl sulfate, sorbitol syrup, cellulose derivatives, hydrogenated edible fats, lecithin, acacia, almond oil, oily esters, ethyl alcohol, fractionated vegetable oils, methyl, propyl-p-hydroxybenzoates, sorbic acid and mixtures thereof. The buffering agents may also comprise at least one of dichlorodifluoromethane, trichloro fluoromethane, dichlorotetra fluoroethane, carbondioxide, poly (N-vinyl pyrrolidone), poly (methylmethacrylate), polyactide, polyglycolide and mixtures thereof.

In another embodiment, the buffering agent is formulated as at least one medium selected from a group, including, but not limited to a suspension, solution, or emulsion. In yet another embodiment, the buffering agent comprises a formulatory agent selected from the group including, but not limited to a carrier, excipient, suspending agent, stabilizing agent and dispersing agent.

It has been discovered that the above-described compositions of the invention may be used to successfully treat a wide range of conditions, diseases and disorders related to conformational changes of proteins from α-helical or random coil to β-sheet conformation. "Treatment" is preferably defined to cover any treatment of a disease in an animal, including a cow, sheep, deer, dog, cat, goat, chicken and turkey, particularly a human, and includes:

a) preventing the disease or symptom from occurring in a subject that may be predisposed to the disease or symptom but has not yet been diagnosed as having it;
 b) inhibiting the disease or its symptom, i.e., arresting development of the disease or symptom; or
 c) relieving the disease or symptom, i.e., causing regression or reversal of the disease or symptom.

The novel compositions of the invention disrupt the abnormal metal ligand/binding site complex of many proteins that cause degenerative diseases so that the protein will remain in its normal soluble state, or solubilize an already assembled or aggregated conformationally altered protein. Amino acid sequences of proteins that cause degenerative diseases are include: βA (FIG. 1; SEQ ID NO 1), APP (FIG. 2; SEQ ID NO 2), PrP (FIG. 3; SEQ ID NO 3), α-Synuclein (FIG. 4; SEQ ID NO 4), Tau (FIG. 5; SEQ ID NO 5), Superoxide Dismutase (FIG. 6; SEQ ID NO 6), and Huntington (FIG. 7; SEQ ID NO 7). Accordingly, the compositions of the invention are used for treating diseases, disorders and conditions manifested by prepathological and pathological protein assembly or aggregation wherein the assembled or aggregated protein contains at least one protein selected from the group consisting of SEQ ID NO 1, SEQ ID NO 2, SEQ ID NO 3, SEQ ID NO 4, SEQ ID NO 5, SEQ ID NO 6, and SEQ ID NO 7.

FIG. 1 shows SEQ ID NO 1, the polypeptide sequence of Beta-Amyloid (βA) as contained in Homo sapiens Beta-Amyloid Precursor Protein (APP$_{770}$) in GenBank Accession No. QRHUA4 from positions 672 to 714. The term "β-amyloid," "β-amyloid peptide" or "βA" refers to a 39–43 amino acid peptide having a molecular weight of about 4.2 kDa, which peptide is substantially homologous to the form of the protein described by Glenner, et al. including mutations and post-translational modifications of the normal β-amyloid peptide (Glenner et al., *Biochem. Biophys. Res. Commun.* 120:885–890 (1984)), and comprising SEQ ID NO: 1, as well as biologically active variants of SEQ ID NO 1, which has at least about 80%, preferably at least about 90%, and more preferably at least about 95%, identity or homology to SEQ ID NO 1 or a biologically active subunit thereof. Biologically active subunits of βA, biologically active variant βA polypeptides, and biologically active subunits thereof, falling within the scope of the invention, have at least about 50%, preferably at least about 80%, and more preferably at least about 90% the activity of the polypeptide comprising SEQ ID NO: 1.

FIG. 2 shows SEQ ID NO 2, the entire polypeptide sequence of APP$_{770}$ in Homo sapiens as listed in GenBank Accession No. QRHUA4. The term "β-Amyloid Precursor Protein" or "APP" refers to a 770 amino acid peptide having a molecular weight of about 87.0 kDa, comprising SEQ ID NO 2 which has at least about 80%, preferably at least about 90%, and more preferably at least about 95%, identity or homology to SEQ ID NO 2 or a biologically active subunit thereof. Biologically active subunits of APP, biologically active variant APP polypeptides, and biologically active subunits thereof, falling within the scope of the invention, have at least about 50%, preferably at least about 80%, and more preferably at least about 90% the activity of the polypeptide comprising SEQ ID NO 2.

FIG. 3 shows SEQ ID NO 3, the polypeptide sequence of Prion Protein in Homo sapiens as listed in GenBank Accession No. XM009567. The term "Prion Protein" or "PrP" refers to a 253 amino acid peptide having a molecular weight of about 27.7 kDa, comprising SEQ ID NO 3 which has at least about 80%, preferably at least about 90%, and more preferably at least about 95%, identity or homology to SEQ ID NO 3 or a biologically active subunit thereof. Biologically active subunits of PrP, biologically active variant PrP polypeptides, and biologically active subunits thereof, falling within the scope of the invention, have at least about 50%, preferably at least about 80%, and more preferably at least about 90% the activity of the polypeptide comprising SEQ ID NO 3.

FIG. 4 shows SEQ ID NO 4, the polypeptide sequence of α-Synuclein in Homo sapiens as listed in GenBank Accession No. XM003494. The term "α-synuclein" refers to a 140 amino acid peptide having a molecular weight of about 14.5 kDa, comprising SEQ ID NO 4 which has at least about 80%, preferably at least about 90%, and more preferably at least about 95%, identity or homology to SEQ ID NO 4 or a biologically active subunit thereof. Biologically active subunits of α-synuclein, biologically active variant α-synuclein polypeptides, and biologically active subunits thereof, falling within the scope of the invention, have at least about 50%, preferably at least about 80%, and more preferably at least about 90% the activity of the polypeptide comprising SEQ ID NO 4.

FIG. 5 shows SEQ ID NO 5, the polypeptide sequence of Tau in Homo sapiens as listed in GenBank Accession No. NM016835. The term "Tau" refers to a 758 amino acid peptide having a molecular weight of about 78.9 kDa, comprising SEQ ID NO 5 which has at least about 80%, preferably at least about 90%, and more preferably at least about 95%, identity or homology to SEQ ID NO 5 or a biologically active subunit thereof. Biologically active subunits of Tau, biologically active variant Tau polypeptides, and biologically active subunits thereof, falling within the scope of the invention, have at least about 50%, preferably at least about 80%, and more preferably at least about 90% the activity of the polypeptide comprising SEQ ID NO: 5.

FIG. 6 shows SEQ ID NO 6, the polypeptide sequence of Superoxide Dismutase in homo sapiens as listed in GenBank Accession No. P00441. The term "superoxide dismutase" refers to a 154 amino acid peptide having a molecular weight of about 15.9 kDa, comprising SEQ ID NO 6 which has at least about 80%, preferably at least about 90%, and more preferably at least about 95%, identity or homology to SEQ ID NO 6 or a biologically active subunit thereof. Biologically active subunits of superoxide dismutase, biologically active variant superoxide dismutase polypeptides and biologically active subunits thereof, falling within the scope of the invention, have at least about 50%, preferably at least about 80%, and more preferably at least about 90% the activity of the polypeptide comprising SEQ ID NO 6. In particular, the biologically active variants of superoxide dismutase can include the Cu—Zn family of superoxide dismutases as well as the Mn family of superoxide dismutases.

FIG. 7 shows SEQ ID NO 7, the polypeptide sequence of Huntingtin in Homo sapiens as listed in GenBank Accession No. XP003405. The term "Huntingtin" refers to a 1543 amino acid peptide having a molecular weight of about 168.8 kDa, comprising SEQ ID NO 7, which has at least about 80%, preferably at least about 90%, and more preferably at least about 95% identity or homology to SEQ ID NO 7, or a biologically active subunit thereof. Biologically active subunits of Huntingtin, biologically active variant Huntingtin polypeptides, and biologically active subunits thereof, falling within the scope of the invention, have at least about 50%, preferably at least about 80%, and more preferably at least about 90% the activity of the polypeptide comprising SEQ ID NO 7.

In accordance with the present invention, diseases caused by biologically active subunits of these proteins may also be treated by administration of the compounds of the invention. The term "biologically active subunit" of a peptide is preferably defined to mean a subunit of a peptide of the invention, including SEQ ID NO 1 through SEQ ID NO 7, which has at least about 10%, preferably at least about 50%, and more preferably at least about 90% activity of a peptide of the invention. A biologically active subunit will have at least one metal-binding site. The activity of a peptide of the invention can be measured by methods well known in the art including, but not limited to the ability of the peptide to bind a transition metal ion in vitro, or the ability of the peptide to change conformation from α-helical or random coil to β-sheet conformation as visualized by changes in optical rotary dispersion (ORD) or circular dichroism (CD), and comparing these results to results obtained from wild-type peptide activity. Accordingly, and in one embodiment of the invention, the above-described compositions are used for treating diseases manifested by prepathological and pathological protein assembly or aggregation of a biologically active subunit of a protein selected from the group consisting of SEQ ID NO 1, SEQ ID NO 2, SEQ ID NO 3, SEQ ID NO 4, SEQ ID NO 5, SEQ ID NO 6, or SEQ ID NO 7.

The term "metal-binding site" is preferably defined to mean a three-dimensional structure comprising at least one amino acid exhibiting steric complementarity between it and a metal ligand, preferably a transition metal ion. Two or more amino acids may form the three-dimensional structure either sequentially connected within a single polypeptide, from different sites within a single polypeptide, or from different polypeptides, exhibiting steric complementarity between it and a metal ligand, preferably a transition metal ion. It is well known in the art that metal ions tend to bind to protein groups for which they have some intrinsic affinity. Thus, both characterized and uncharacterized metal binding sites of SEQ ID NO 1 through SEQ ID NO 7 that can be predicted by methods well known in the art, e.g., by using computer software techniques or chemosensors, are within the scope of the invention.

For example, it is well known in the art that Zn(II) ions tend to be bound to sulfur atoms and to the imidazole nitrogen atoms of His residues; Fe(II) and Fe(III) to the sulfur atoms of Cys residues or to sulfide ions and in iron-sulfur proteins; Ca(II) ions tend to interact with thiol or imidazole groups; Ca(II) ions tend to be bound to oxygen atoms; and, Mg(II) ions are bound along with the phosphate groups of ligands. In addition, metal-binding site sequences, including but not limited to Zn-finger, Fe-finger, and Fe-ring structures, may be predicted by chemosensors such as those described in U.S. Pat. No. 6,083,758 to Imperiali, et al., herein incorporated by reference in its entirety.

Computer software using predictive algorithms may also be used to determine the existence of a metal-binding site. Data representing the intrinsic metal-binding affinities of certain amino acids in cooperative conformations can be used by the algorithm to predict the amino acids comprising a metal-binding site and the affinity for metal ligands.

The activity of a metal-binding site of the invention can be measured by methods well known in the art including, but not limited to the ability of the peptide to bind a transition metal ion in vitro, or the ability of the peptide to change conformation from α-helical or random coil to β-sheet conformation as visualized by changes in ORD or CD spectrum, and comparing these results to results obtained from wild-type peptide activity.

The metal-binding sites of these proteins will be present in certain biologically active subunits and/or biologically active variants of the proteins of FIG. 1 through FIG. 7 (SEQ ID NO: 1 through SEQ ID NO 7). The use of the compositions of the invention to treat diseases manifested by the assembly or aggregation of these biologically active subunits and/or biologically active variants is intended to fall within the scope of the invention. Therefore, the protein targets of the invention include proteins having at least about 80%, preferably at least 90%, and more preferably at least about 95% identity to the above disclosed proteins of FIG. 1 through FIG. 7 (SEQ ID NO 1 through SEQ ID NO 7).

The following Table is a non-exclusive list of diseases, disorders and conditions, and their associated proteins, that assume two or more different protein conformations, one of which causes a manifestation of the disease.

| Disease | Insoluble Proteins |
|---|---|
| Alzheimer's Disease | APP, βA, α1-antichymotrypsin, tau, non-βA component |
| Prion Diseases, Creutzfelds-Jakob disease, scrapie and bovine spongiform encephalopathy | PrP$^{Sc}$ |
| ALS | SOD and neurofilament |
| Pick's Disease | Pick body |
| Parkinson's Disease | α-synuclein in Lewy bodies |
| Frontotemporal dementia | Tau in neurofibrillary tangles |
| Type II Diabetes | Amylin |
| Multiple myeloma-plasma cell dyscrasias | IgG L-chain |
| Familial amyloidotic polyneuropathy | Transthyretin |
| Medullary carcinoma of thyroid | Procalcitonin |
| Chronic renal failure | B$_2$-microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |
| Huntington's Disease | Huntingtin |

In accordance with the present invention, diseases caused by biologically active variants of the above proteins are also treated by the introduction of the composition of the invention to the variants. The term "biologically active variant" of a protein is preferably defined to mean a protein, which has at least about 80%, preferably at least about 90%, more preferably 95% identity or homology to a protein of the invention, including SEQ ID NO 1 through SEQ ID NO: 7. Biologically active variants of the peptides of the invention have at least about 10%, preferably at least 50%, and more preferably at least about 90% activity of a protein of the invention. A biologically active subunit will have at least one metal-binding site. The activity of a variant peptide or protein of the invention can be measured by methods well known in the art including, but not limited to the ability of the peptide to bind a transition metal ion in vitro, or the ability of the peptide to change conformation from α-helical or random coil to β-sheet conformation as visualized by changes in ORD or CD, and comparing these results to results obtained from wild-type peptide activity. Therefore, the compounds of the invention may be used for treating diseases manifested by prepathological and pathological protein assembly or aggregation of a biologically active variant of a protein selected from the group consisting of SEQ ID NO 1, SEQ ID NO 2, SEQ ID NO 3, SEQ ID NO 4, SEQ ID NO 5, SEQ ID NO 6, or SEQ ID NO 7.

Many of the above proteins are metalloproteins that play a role similar to metalloproteins in cancers, pain, inflammation, proliferative and infectious diseases. It is well known that metalloproteins that change conformation by binding a transition metal ion can activate certain enzymes, viruses and cancers. For example, metal-binding site motifs, such as zinc-finger or zinc-ring sequences, play an important role as hormone-receptor proteins and in proliferative, inflammatory and infectious diseases. Inhibition of zinc-finger proteins results in potent anti-cancer and anti-viral effects in vivo. The effect of picolinic acid and fusaric acid, and their analogs or derivatives, on cancers and viruses is detailed in U.S. Pat. Nos. 6,127,393 and 5,767,135, herein incorporated by reference in their entireties.

Proteins having metal-binding sites, particularly those sites complementary to transition metal ions, appear to be effective targets for treatment of diseases caused by conformational alteration of these proteins. Different conformations of the same proteins, having the same primary amino acid sequence, can have dramatically different activities in vivo. For example, AD and PrP infection are believed to be caused by transition metal ion related conformation changes from normally soluble α-helical or random coil to insoluble β-sheet structures. Accordingly, disrupting the metal binding and β-sheet formation of the proteins underlying these diseases is an effective mode of treating the diseases.

Zn-, Cu- and/or Fe-binding sites on βA and PrP are required for the assembly and aggregation of proteins causing Alzheimer's Disease, FAD, CAA, spongiform encephalopathies and prion diseases which include kuru, CJD, Gerstmann-Straussler-Sheinker Disease (GSS), fatal familial insomnia (FFI) and related scrapie diseases. It is also believed that metal-binding sites exist within other proteins manifesting in diseases related to the prepathological and pathological assembly or aggregation of the proteins. Such pathologies include: Parkinson's disease, frontal temporal dementia, Pick's disease, amyotrophic lateral sclerosis and Huntington's disease. Other diseases manifested by the assembly or aggregation of conformationally altered proteins, including the proteins of FIG. 1 through FIG. 7 (SEQ ID NO: 1 through SEQ ID NO 7), requiring Zn, Cu and/or Fe to assemble and/or aggregate can be successfully treated by the introduction of the compositions of the invention to those conformationally altered proteins. Thus, an effective treatment of these diseases, involving abnormal metal-binding and prepathological and pathological protein assembly or aggregation, is administering the compositions of the invention to disrupt, or interfere with, the formation or action of these metal-binding proteins to prevent, inhibit, stop, and/or reverse the progress of the related diseases. Accordingly, and in one embodiment of the invention, conformationally altered protein assembly or aggregation in an animal is reversed or prevented by introducing the above-described compositions of the invention to the conformationally altered protein. In a specific embodiment, picolinic acid, its analogs, or derivatives is introduced to the conformationally altered protein. In another specific embodiment, fusaric acid is introduced to the conformationally altered protein.

In one embodiment of the invention, Alzheimer's Disease is treated by the introduction or administration of the compositions of the invention to the affected animal. AD is a progressive neurodegenerative disorder characterized by extracellular deposits of βA, the main component of neuritic or senile and diffuse plaques. The βA$_{1-40}$ isoform is the predominant soluble species in biological fluids. Although less abundant in biological fluids, βA$_{1-42}$ is found in higher concentrations in plaque deposits.

Pathogenic mutations of the APP gene close to or within the βA domain are linked to forms of FAD. Inheritance of mutations on chromosome 14 (presenilin-1), or chromosome 1 (presenilin-2) produces the more aggressive form of the disease manifesting in early-onset at age 25 to 45 years. Under normal physiological conditions, βA is a soluble cellular metabolite that is produced by a variety of cells and is found in the cerebrospinal fluid and plasma. However, βA in the neuritic or senile and diffuse plaques is in the form of amyloid fibrils that are insoluble under physiological conditions. It is likely that neurochemical factors, having levels altered through the course of aging, initiate βA deposition in sporadic AD and FAD. Thus, the plaque deposits of βA appear to be a morphological variation of βA accumulation caused by neurochemical interactions that are specific to the neocortex. The availability of high concentrations of Cu(II) and Zn(II) is a specific feature of neocortical tissue that explains the condensation of βA as plaque.

βA deposition in the neocortex is closely related to the pathology of AD. The deposition of βA in the neocortex of APP transgenic mice overexpressing βA is accompanied by some neuropathological features of AD such as neuronal loss suggesting that the neurotoxic events of AD are related to βA accumulation. In addition, many studies have now confirmed that βA is neurotoxic in cell culture and in vivo.

A consensus has emerged among researchers that the homeostases of Zn(II), Cu(II), and Fe(III) are significantly altered in AD brain tissue. For example, abnormal levels of Zn(II), Cu(II), or Fe(III) have been found in several sub-cortical regions such as the hippocampus, amygdala, and olfactory bulb, as well as the neocortex.

Synthetic βA and purified APP exhibit several physicochemical interactions with Zn(II), Cu(II), and to a lesser extent Fe(III), at low micromolar and submicromolar concentrations of the metal ions. Although the transition metal ions Zn, Cu, and Fe are maintained at high concentrations within the healthy brain neocortical parenchyma, increased concentrations of these metal ions are detected in the neuropil of the AD-affected brain, where they are highly concentrated within amyloid plaque deposits. An elevated Zn(II) concentration can also be detected in plaque deposits histologically. βA has also been found to avidly bind Zn(II), Cu(II), and Fe(III) in vitro, suggesting that these metals are an important factor in amyloid plaque pathology.

The roles these metal ions play in cerebral amyloid assembly and aggregation have been further characterized by experiments showing that Zn(II)- and Cu(II)-selective chelators enhance the solubilization of βA collections in postmortem brain specimens from AD subjects and from amyloid precursor protein transgenic mice. Specific and saturable Zn-binding sites have been identified at positions 181–200 and 135–155 of $APP_{695}$ ($APP_{181-200}$ and $APP_{135-155}$) of FIG. 2 (SEQ ID NO 2). Additional Zn- and Cu-binding sites have been found at positions 108, 110, 147, 149, 151, 183, 186, and 187 of $APP_{770}$. FIG. 2 (SEQ ID NO 2) below is the entire 770 amino acid sequence of $APP_{770}$ that contains the $APP_{695}$ splice form by connection of positions 1–288 and 365–770. These sites have homology in all known members of the APP superfamily. This indicates that Zn and Cu interaction with the protein may play an important, evolutionary conserved role in APP function and metabolism.

$βA_{1-40}$ specifically and saturably binds Zn(II), Cu(II) and Fe(III). The His residue, at position 13 of FIG. 1 (SEQ ID NO 1), is believed to be an important residue in Zn-mediated βA assembly. The His residue, at position 14 of FIG. 1 (SEQ ID NO 1), is also an important residue in Zn-mediated βA assembly. The entire Zn-binding site between positions 6 and 28 of FIG. 1 (SEQ ID NO 1) has been characterized.

Further three dimensional analysis of βA residues 11–25, believed to be the core domain of the βA fibril, have also been resolved, suggesting that βA in plaques take a β-hairpin conformation in one species of the β-sheet conformation in AD. It is believed that multiple β-hairpin fragments further form a protofilament, or stacking of βA β-hairpin units, and later assemble to form the neurotoxic plaque with five or six protofilaments forming a hollow tube, or β-sheet crystallite. Both βA and a fragment of the Prion Protein (PrP) exist in a pentagonal or hexagonal array of β-sheet crystallites.

The $βA_{1-42}$ isoform was discovered to initiate aggregation and assembly of $βA_{1-40}$. It was also determined that the addition of Zn(II), Cu(II), and Fe(III) both enhance and are required for the $βA_{1-42}$-initiated seeding of $βA_{1-40}$. Both Zn- and Cu-induced aggregation and assembly of $βA_{1-40}$ is reversible by chelation with strong Zn/Cu chelators such as N,N,N',N'-tetrakis-(2-pyridylmethyl)-ethylenediamine and bathocuproine disulfonic acid in vitro. Thus, solubilization of βA plaque may be accomplished by chelating the Zn, Cu, and Fe bound to βA. Such Zn/Cu chelators, however, exhibit toxic effects in vivo and are not believed to be able to pass the blood-brain barrier upon administration by inhalation, insufflation, oral, buccal, parenteral, transdermal, or rectal administration.

The PrP gene in mammals expresses a protein that can be either a soluble, non-disease form ($PrP^C$), or in an insoluble, disease causing form ($PrP^{Sc}$). $PrP^C$ is encoded by a single-copy host gene and is generally found on the outer surface of neurons. FIG. 3 (SEQ ID NO 3) shows the translated product of the single-copy gene in Homo sapiens. It is thought that prion diseases result from the transformation of $PrP^C$ into $PrP^{Sc}$ by changing from an α-helical conformation to a β-sheet conformation. Currently, the only disease-specific diagnostic marker of prion diseases is the presence of $PrP^{Sc}$ in the brains of infected animals, including humans. Although there is no difference in the primary amino acid sequence of the two forms, $PrP_{Sc}$ has a conformation with higher β-sheet and lower α-helix or random coil content than $Pr_{Pc}$. Transition metal ions are believed to be required for the conformation change.

$PrP^{Sc}$ plays a key role in both transmission and pathogenesis of prion diseases (e.g., spongiform encephalopathies) and it is a critical factor in neuronal degeneration. Four prion diseases of humans have been identified: kuru, CJD, GSS, and FFI. The most common prion diseases in animals are scrapie in sheep and goats and bovine spongiform encephalopathy (BSE) in cattle. These diseases are thought to be able to spread across species to other hoofed animals, such as deer, and potentially other staple animals such as chickens, turkeys, dogs and cats. At the time of the invention, scrapie and related diseases have caused billions of dollars in damage related to enacting quarantine procedures and destroying livestock suspected of being infected with PrP. There is currently no treatment for these diseases.

It will be appreciated by those skilled in the art that other diseases, including, but not limited to Parkinson's disease, frontal temporal dementia, Pick's disease, amyotrophic lateral sclerosis, and Huntington's disease, that are caused by assembly or aggregation of conformationally altered proteins, and that comprise SEQ ID NO 4 through SEQ ID NO 7 (FIG. 4 through FIG. 7) contain at least one metal-binding motif that can be predicted by methods well known in the art, e.g., by using computer software techniques or chemosensors. The treatment of the aforementioned diseases manifested by assembly or aggregation of the above-described proteins, biologically active subunits and biologically active variants thereof by the introduction of the compositions of the invention to the conformationally altered protein is intended to be within the scope of the invention.

In vitro studies reveal that picolinic acid and fusaric acid have activity in cell-free systems that allow examination of the formation and reversal of formation of βA fibrillar deposits. CD spectroscopy and electron microscopy have previously shown that Zn is required for conformational changes of βA.

CD spectroscopy is based on the principle that the L-amino acids in polypeptides and proteins interact differently with beams of left-and right-circularly polarized light, which causes the beams to travel at different speeds through these molecules, thereby rotating the polarized light. Left- and right-circularly polarized beams of light are also absorbed to different extents by chiral molecules. Relative amounts of random coiled, α-helix and β-sheet conformations are readily resolved by comparing CD absorption bands to control data. For example, the absorption spectra for an oligopeptide such as poly(Lys) show distinctive absorption spectra for the random coil, α-helix and β-sheet conformations of the polypeptide:

Random coil: Minima of about −40 degree cm$^2$/decimole at about 197 nm. Maxima of about 5 degree cm$^2$/decimole at about 218 nm.

α-helix: Minima of about −32 and −35 degree cm$^2$/decimole at about 208 and 222 nm respectively. Maxima of about 78 degree cm$^2$/decimole at about 192 nm.

β-sheet: Minima of about −18 degree cm$^2$/decimole at about 218 nm. Maxima of about 32 degree cm$^2$/decimole at about 195 nm.

The compositions of the invention described herein are administered to a patient at a therapeutically effective dose to treat or ameliorate neurodegenerative disorders, e.g., amyloidoses, prion diseases, and other degenerative diseases. The term "therapeutically effective" dose is preferably defined to mean an administration of the compounds of the invention sufficient to provide the desired physiological and/or psychological change. This will vary depending on the patient, the disease and the treatment. The dose may either be a therapeutic dose, in which case it sufficiently alters levels of conformationally altered protein deposits in the subject to alleviate or ameliorate the symptoms of the disorder or condition, or a prophylactic dose, which is be sufficient to prevent accumulation of insoluble protein deposits to an undesired level.

Toxicity and therapeutic efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the methods of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The dosage also depends on the patient and condition being treated and on the administration route. For example, the dosage depends upon the efficacy of a therapeutic effect for different mammals, often requiring widely varying doses, and the mode of administration, e.g., oral doses may often be ten times the injection dose because of the degradation of a compound that may occur in the stomach.

Pharmaceutical compositions for use in the invention can be formulated in a conventional manner using one or more pharmaceutically acceptable carriers or excipients. Thus, the compositions of the invention can be formulated for administration by inhalation, insufflation (either through the mouth or the nose), oral, buccal, parenteral, transdermal, or rectal administration.

For oral administration, the pharmaceutical compositions can take the form of, for example, tablets or capsules prepared by conventional means with pharmaceutically acceptable excipients including, but not limited to binding agents, e.g., pregelatinized maize starch, polyvinylpyrrolidone or hydroxypropyl methylcellulose; fillers, e.g., lactose, microcrystalline cellulose or calcium hydrogen phosphate; lubricants, e.g., magnesium stearate, talc or silica; disintegrants, e.g., potato starch or sodium starch glycolate; and, wetting agents, e.g., sodium lauryl sulfate. The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives including, but not limited to suspending agents, e.g., sorbitol syrup, cellulose derivatives or hydrogenated edible fats; emulsifying agents, e.g., lecithin or acacia; non-aqueous vehicles, e.g., almond oil, oily esters, ethyl alcohol or fractionated vegetable oils; and preservatives, e.g., methyl or propyl-p-hydroxybenzoates or sorbic acid. The preparations can also contain buffering agents, flavoring, coloring and sweetening agents as appropriate. Preparations for oral administration can be suitably formulated to give controlled release of the active compound, e.g., time release formulations for predetermined dosage release over predetermined time periods. For buccal administration, the compositions can take the form of tablets or lozenges formulated in a conventional manner.

For administration by inhalation, the compositions of the invention are conveniently delivered in the form of an aerosol spray presentation from pressurized packs or a neubulizer, with the use of a suitable propellant, e.g, dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator, can be formulated containing a powder mix of a compound of the invention and a suitable powder base such as lactose or starch.

The compositions of the invention can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compositions of the invention can be formulated for transdermal administration in the form of permeable membranes placed directly on the stratum corneum (i e., the outer most layer of skin). Formulations for transdermal administration can include suitable carriers, e.g., poly(N-vinyl pyrrolidone), poly(methyl methacrylate), polylactides, and polyglycolides. The permeation of drugs through skin can also be enhanced by physical methods such as iontophoresis (i.e., application of low level electric current), phonophoresis (i.e., use of ultra sound energy) and by chemical penetration enhancers, e.g., fatty acids, fatty alcohols and terpenes.

The compositions of the invention can also be formulated in rectal compositions such as suppositories or retention enemas, e.g., containing conventional suppository bases such as cocoa butter or other glycerides. In addition to the formulations described previously, the compositions can also be formulated as depot preparations. Such long acting formulations can be administered by implantation, for example, subcutaneously or intramuscularly, or by intramuscular injection. Thus, for example, the compounds can be formulated with suitable polymeric or hydrophobic materials, e.g., as an emulsion in an acceptable oil, or ion exchange resins, or as sparingly soluble derivatives, for example as a sparingly soluble salt.

The compositions of the invention can, if desired, be administered in a pack or dispenser device that can contain one or more unit dosage forms containing the active ingredient. The pack can for example comprise metal or plastic foil, such as a blister pack. In addition, the compositions may be administered in an ampoule or multi-dose container. The pack or dispenser device can be accompanied by instructions for administration.

The following examples are illustrative of specific embodiments of the invention and do not limit the scope of the invention in any way.

EXAMPLE 1

Zn-mediate βA Polymer Formation and its Reversal by Picolinic or Fusaric Acid

Negative stain electron microscopy (EM) reveals Zn-induced polymerization and fibril formation of $\beta A_{1-40}$ and the effect of fusaric acid and picolinic acid as seen in FIGS. 8 through 14. $\beta A_{1-40}$ may be prepared by in vitro methods well known in the art, such as solid phase protein synthesis or t-Boc and CBZ protein synthesis. See Tarbell, D. S., Yamamoto, Y. & Pope, B. M. *Proc. Natl. Acad. Sci. USA* 69, 730–732 (1972), herein incorporated by reference in its entirety. The peptide was purified by C18 reverse phase HPLC and lypholized. Lypholized peptides were then dissolved in aqueous buffers such as phosphate buffered saline (PBS). High purity of the peptides was determined by mass spectrometry and quantitative amino acid analysis.

When $\beta A_{1-40}$ was incubated in PBS at 37° C. in the presence of 10 μM Zn acetate at pH 6.5, it formed lateral polymers and fibril aggregates. FIG. 8 shows $\beta A_{1-40}$ incubated in the presence of Zn at a magnification of 1:52,000. These lateral fibrils are formed de novo upon adding Zn to the solution containing soluble $\beta A_{1-40}$. These lateral fibril aggregates are reversible and require the presence of Zn for formation. Peptides were then diluted to a final concentration of 300 μM in aqueous buffers with the Zn concentration adjusted to 3 mM for 2 hours. For negative staining, 10 μl of each sample was applied to Pioloform® (Wacker Polymer Systems, GmbH, Germany) and carbon-coated grids, blotted with filter paper and stained with 1% (w/v) phosphotungstic acid having a pH of 7.0. The specimens were examined on a Hitachi H7000 electron microscope (Hitachi Corp., Japan) with an accelerating voltage of 75 kV.

Figure 9:
FIG. 9 illustrates the $βA_{1-40}$ fibrils of FIG. 8 incubated with fusaric acid at a magnification of 1:52,000.
Figure 10:
FIG. 10 illustrates the $βA_{1-40}$ fibrils of FIG. 8 incubated with picolinic acid at a magnification of 1:52,000.
Figure 11:
FIG. 11 illustrates $βA_{1-40}$ fibrils in the presence of fusaric acid at a magnification of 1:52,000 becoming solubilized and forming fibril debris.
Figure 12:
FIG. 12 illustrates $βA_{1-40}$ fibrils in the presence of picolinic acid at a magnification of 1:52,000 becoming solubilized and forming fibril debris.

Polymerization and fibril formation was prevented by incubation of the mixture under identical conditions in the presence of 100 μM picolinic or fusaric acid. FIG. 9 shows the $\beta A_{1-40}$ fibrils of FIG. 8 incubated with fusaric acid at a magnification of 1:52,000. No additional Zn-mediated polymerization of $\beta A_{1-40}$ fibrils was observed upon incubation with fusaric acid. FIG. 10 shows the $\beta A_{1-40}$ fibrils of FIG. 8 incubated with picolinic acid at a magnification of 1:52,000. No additional Zn-mediated polymerization of $\beta A_{1-40}$ fibrils was observed upon incubation with picolinic acid. In addition, when preformed fibrils (formed in the presence of Zn) were incubated with picolinic or fusaric acid, the fibril aggregates dissociated. FIG. 11 shows the $\beta A_{1-40}$ fibrils in the presence of fusaric acid at a magnification of 1:52,0000 becoming solubilized and forming fibril debris. FIG. 12 shows the $\beta A_{1-40}$ fibrils in the presence of picolinic acid at a magnification of 1:52,0000 becoming solubilized and forming fibril debris. This indicates that both picolinic and fusaric acid are able to prevent the formation of conformationally altered $\beta A_{1-40}$ polymerization, which requires zinc binding and to disassociation of bound Zn, thereby causing conformational changes in $\beta A_{1-40}$ and resulting in reversal of $\beta A_{1-40}$ polymerization.

EXAMPLE 2

Reversal of βA Aggregation by Changing Protein Conformation

CD spectroscopy demonstrates that picolinic acid and fusaric acid prevent and reverse $\beta A_{1-40}$ fibril formation by changing the conformational structure of the protein. $\beta A_{1-40}$ was solubilized in filtered 20 mM sodium phosphate buffer having a pH of 7.0 to a final peptide concentration of 55 μM. Zn(II) was added to $\beta A_{1-40}$ in 20 mM Tris buffer having a pH of 7.0 at a molar ratio of 1:10. The samples were allowed to stand for 10 minutes at room temperature prior to analysis. CD spectra were then acquired on a Jasco spectropolarimeter Model J-715 (Jasco Corp., Japan) at room temperature in a 0.1-cm path length cell over the wavelength range 190–250 nm with a 1.0 nm bandwidth, 0.1 nm resolution, 1 second response time and 20 nm/minute scan rate.

Figure 13:
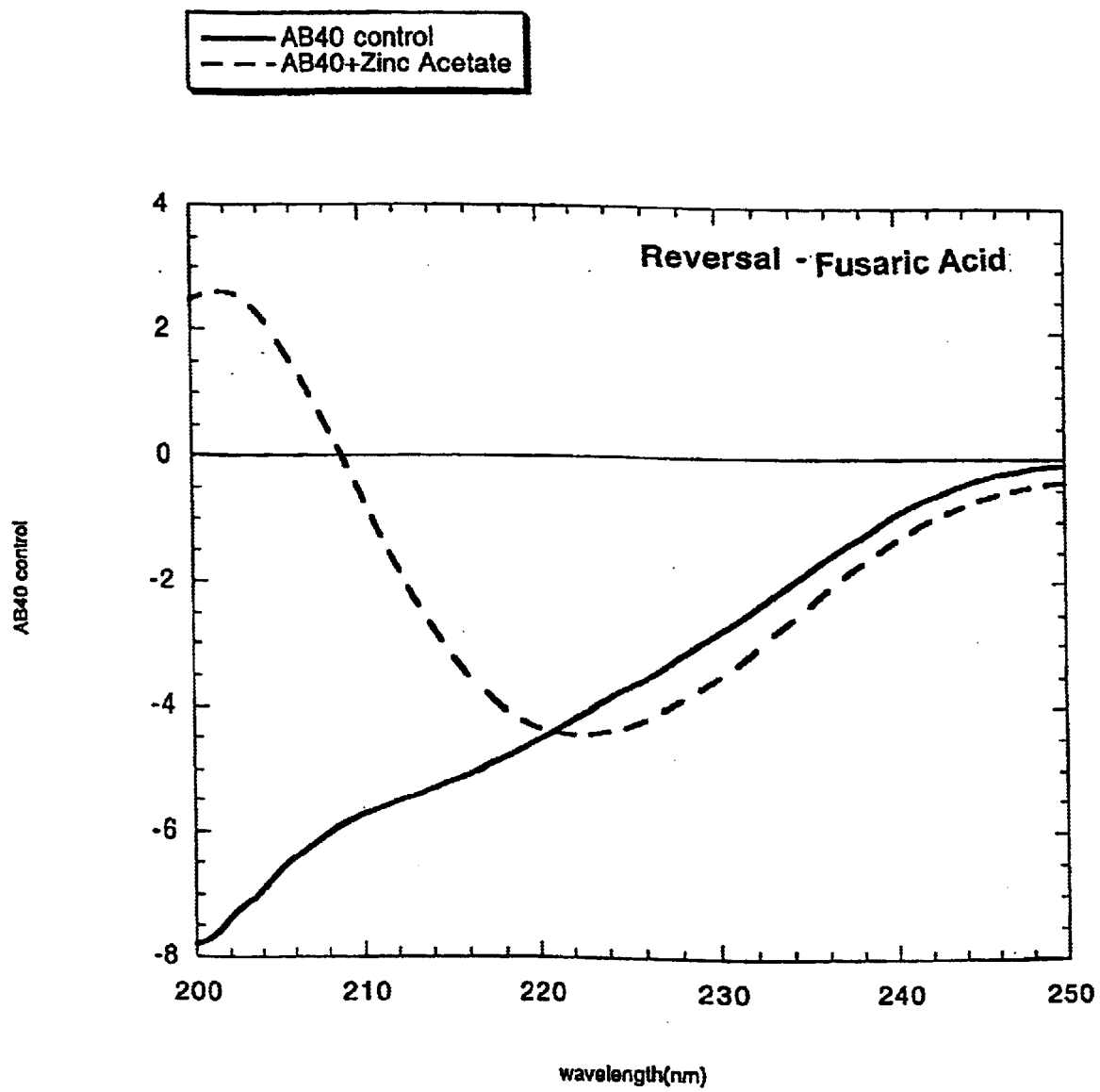
FIG. 13 illustrates a circular dichroism absorbance spectrum of a $βA_{1-40}$ solution upon addition of Zn.
Figure 14:
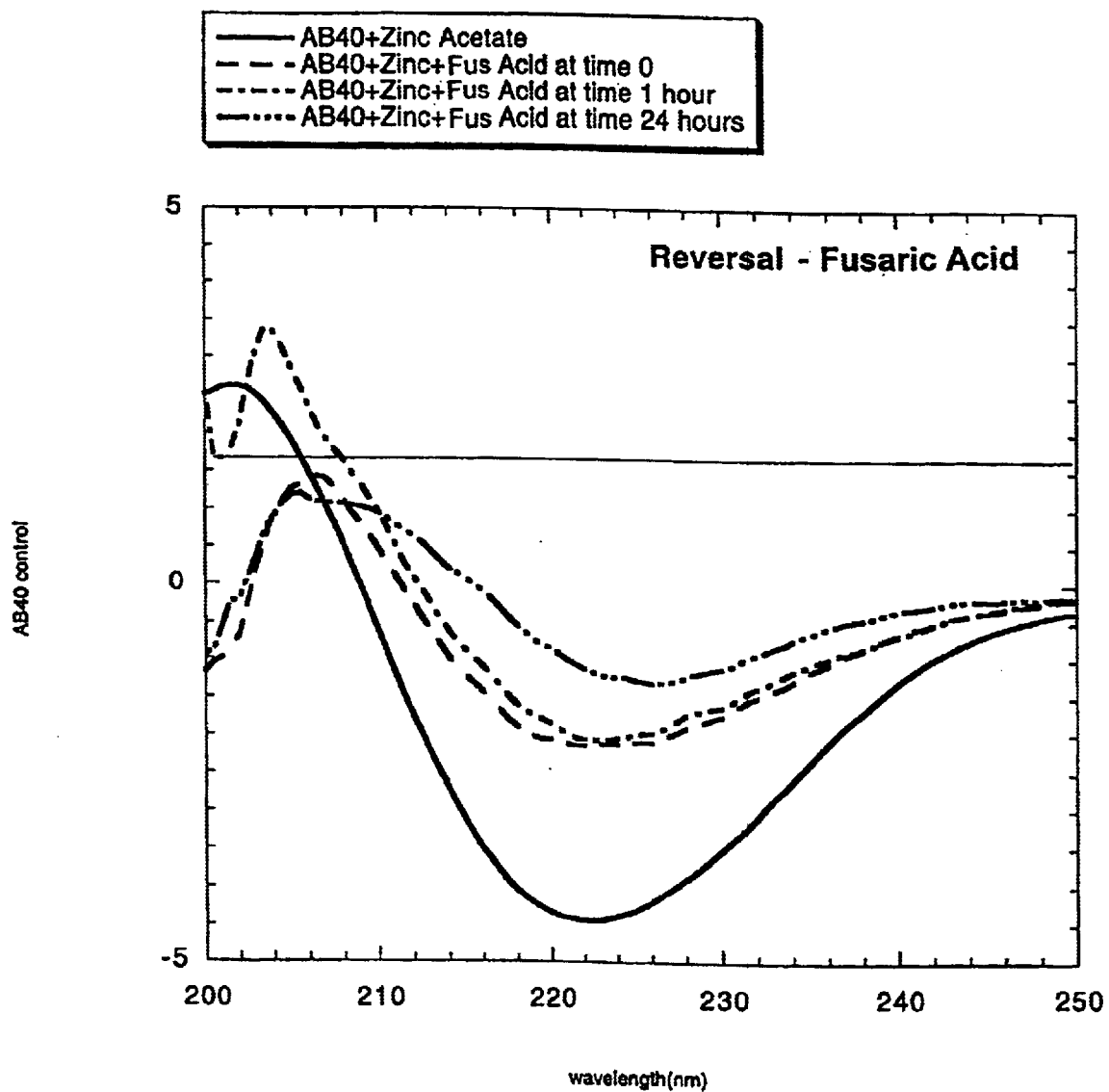
FIG. 14 illustrates a circular dichroism absorbance spectrum of a $βA_{1-40}$ solution and the reduction of β-sheet conformation upon incubation with fusaric acid.

The β-sheet conformation is demonstrated by the presence of absorbance maxima at 202 nm. FIG. 13 shows a CD absorbance spectrum of a $\beta A_{1-40}$ solution upon addition of Zn. The x-axis is measured in nm and the y-axis is measured in degree $cm^2$/decimole. The formation of the $\beta A_{1-40}$ β-sheet conformation is confirmed by observing the formation of a peak at approximately 202 nm. However, in the presence of a small molar excess of picolinic acid or fusaric acid, the Zn-dependent conversion of the $\beta A_{1-40}$ from the random coil to the β-sheet conformation is prevented as seen by the decrease of the 202 nm peak. FIG. 14 shows a CD absorbance spectrum of a $\beta A_{1-40}$ solution and the reduction of the β-sheet conformation upon incubation with fusaric acid. The reduction can be seen by observing the decreasing peak at approximately 202 nm from hour 0, to hour 1, to hour 24. Once the β-sheets of $\beta A_{1-40}$ are formed in the presence of Zn, they are reversed by the addition of either picolinic acid or fusaric acid. The loss of β-sheet conformation is due to Zn sequestration by picolinic acid or fusaric acid. Thus, the reversal of protein aggregation by picolinic acid and fusaric acid is directly linked to the ability to alter protein conformation by disrupting, or interfering with, Zn binding to the Zn-binding site. This change in protein conformation results in the prevention and reversal of protein fibril formation and solubilization of fibrils and aggregates.

EXAMPLE 3

Release of βA from Human Brain Tissue

A series of picolinic acid and fusaric acid incubations show that picolinic and fusaric acid release βA directly from brain slices from post mortem AD patients. Small amounts of brain tissue were bathed in a predetermined volume of physiological buffer solution containing either 1 mM picolinic acid or fusaric acid for 8–12 hours at 4° C. with gentle mixing. At the end of the incubation, the amount of amyloid protein released from the tissue was quantitated using Enzyme-Linked Immunosorbent Assay (ELISA) techniques well known in the art and a monoclonal antibody specific for $\beta A_{1-40}$.

Human brain tissue from deceased Alzheimer's dementia patients was used to determine the activity of picolinic and fusaric acids in the release of βA from neurofibrillar plaques present in abundance in this tissue. This study was performed to demonstrate the reversal of full-length plaque protein due to βA deposition formed in vivo. After incubation under physiological conditions, the amount of specific βA solubilized and released from the brain tissue was quantitated using an immunoassay with an antibody specific the βA. Data from a representative ex vivo study is shown in TABLE 2. The data indicate that picolinic acid and fusaric acid mediate the release of full length βA formed in vivo from human brain tissue slices.

TABLE 2

Release of β-Amyloid Protein from Human Brain Tissue by Various Agents

| Condition | Patient AD2 set 1 (cts × 10⁻³) | Patient AD2 set 2 (cts × 10⁻³) |
| --- | --- | --- |
| Blank | 313 | 358 |
| Fusaric acid, 1 mM | 450 | 449 |
| Picolinic Acid, 1 mM | 422 | 416 |
| EDTA, 1 mM | 256 | 325 |

This representative data indicates that both fusaric acid and picolinic acid promote the release of βA from plaques in human brain tissue that is greater than that released by the well-characterized chelator EDTA.

Although preferred embodiments of the invention have been described in the foregoing Detailed Description of the Invention, it will be understood that the invention is not limited to the embodiments disclosed but is capable of numerous modifications without departing from the spirit and scope of the present invention.

---

What is claimed is:

1. A method of preventing or reversing conformationally altered protein assembly or aggregation in an animal, comprising:

administering to the animal a compound of the following structure:

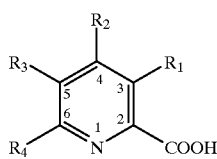

wherein $R_1$, $R_2$, $R_3$ and $R_4$ are selected from a group consisting of an oligopeptide carboxyl group, methyl group, ethyl group, propyl group, isopropyl group, butyl group, isobutyl group, secondary butyl group, tertiary butyl group, pentyl group, isopentyl group, neopentyl group, fluorine, chlorine, bromine, iodine and hydrogen, thereby preventing or reversing confromationally altered protein assembly or aggregation.

2. The method of claim 1, wherein $R_3$ is a butyl group.

3. The method of claim 1, wherein said conformationally altered protein is at least one protein selected from a group consisting of SEQ ID NO 1, SEQ ID NO 2, SEQ ID NO 3, SEQ ID NO 4, SEQ ID NO 5, SEQ ID NO 6 and SEQ ID NO 7.

4. The method of claim 1, wherein said protein contains a biologically active variant of at least one protein selected from a group consisting of SEQ ID NO 1, SEQ ID NO 2, SEQ ID NO 3, SEQ ID NO 4, SEQ ID NO 5, SEQ ID NO: 6 and SEQ ID NO 7.

5. The method of claim 1, wherein the picolinic acid, analogs or derivatives, is administered to an animal by injection.

6. The method of claim 1, wherein the picolinic acid, analogs or derivatives, is administered to an animal orally.

7. The method of claim 1, wherein the picolinic acid, analogs or derivatives, is adminsitered to an animal buccally.

8. The method of claim 1, wherein the picolinic acid, analogs or derivatives, is administered to an animal parenterally.

9. The method of claim 1, wherein the picolinic acid, analogs or derivatives, is administered to an animal transdermally.

10. The method of claim 9, wherein the administration comprises placing a permeable membrane in fluid communication with a solution comprising said picolinic acid, its analogs or derivatives, directly on the skin of said animal.

11. The method of claim 9, wherein the step of administering picolinic acid, its analogs, or derivations to an animal transdermally is enhanced by methods selected from a group consisting of iontophoresis, phonophoresis and by chemical penetration enhancers selected from a group consisting of fatty acids, fatty alcohols and terpenes.

12. The method of claim 1, wherein the picolinic acid, its analogs or derivatives, is administered to an animal rectally.

13. The method of claim 12, comprising administering a solution comprising picolinic acid, its analogs or derivatives, in combination with a glyceride, by suppository into the rectum of said animal.

14. The method of claim 1, wherein the picolinic acid, its analogs or derivatives, is administered as a depot preparation.

15. The method of claim 14, comprising administering said picolinic acid, or an analog or derivative thereof by implantation or intramuscularly injecting a solution comprising picolinic acid, its analogs or derivatives, in combination with a polymeric or hydrophobic material.

16. The method of claim 15, comprising administering said picolinic acid, its analogs, or derivatives by implantation or intramuscularly injecting a solution comprising picolinic acid, its analogs, or derivatives, in combination with a polymeric material, wherein the polymeric material is at least one selected from a group consisting of an emulsion in an oil and an ion exchange resin.

17. The method of claim 15, comprising administering said picolinic acid, its analogs, or derivatives by implantation or intramuscularly injecting a solution comprising picolinic acid, its analogs, or derivatives, in combination with a hydrophobic material, wherein the hydrophobic material is a sparingly soluble salt of a picolinic acid anion, analogs or derivatives thereof.

18. The method of claim 1, further comprising disrupting a metalloprotein complexed with a transition metal ion and at least one protein sequence selected from a group consisting of SEQ ID NO 1, SEQ ID NO 2, SEQ ID NO: 3, SEQ ID NO 4, SEQ ID NO 5, SEQ ID NO 6 and SEQ ID NO 7.

19. The method of claim 1, further comprising disrupting a metalloprotein complexed with a transition metal ion and a biologically active variant of at least one protein selected from a group consisting of SEQ ID NO 1, SEQ ID NO 2, SEQ ID NO 3, SEQ ID NO 4, SEQ ID NO 5, SEQ ID NO 6 and SEQ ID NO 7.

20. A method of preventing or reversing conformationally altered protein assembly or aggregation in an animal comprising administering to the animal a composition comprising fusaric acid, thereby preventing or reversing conformationally altered protein assembly or aggregation.

21. A method of treating conformationally altered protein assembly or aggregation in an animal comprising:

administering to the animal a therapeutically effective amount of a compound represented by the following structure:

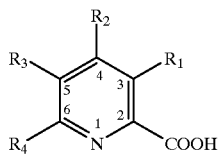

wherein $R_1$, $R_2$, $R_3$ and $R_4$ are selected from a group consisting of an oligopeptide, carboxyl group, methyl group, ethyl group, propyl group, isopropyl group, butyl group, isobutyl gorup, secondary butyl group, tertiary butyl group, pentyl group, isopentyl group, neopentyl group, fluorine, chlorine, bromine, iodine and hydrogen, thereby preventing or reversing confromationally altered protein assembly or aggregation.

22. The method of claim 21 wherein $R_3$ is a butyl group.

23. The method of claim 21, wherein the administration of said therapeutically effective amount of said composition comprises:

administering said therapeutically effective amount of said composition to cells within said animal.

24. The method of claim 23, wherein the administration of said therapeutically effective amount of said composition to cells comprises:

administering the composition to cells which are within an animal selected from a group consisting of a human, a cow, a sheep, a deer and a goat.

25. The method of claim 24, wherein the administration of said therapeutically effective amount of said composition to cells within a human comprises:

administering the composition to brain tissue cells within said human.

26. The method of claim 21, further comprising adding said therapeutically effective amount of said compound to a treatment regimen of at least one or more therapeutic agents.

27. The method of claim 21, wherein the conformationally altered proteins assembly or aggregation is caused by a disease selected from a group consisting of Alzheimer's disease, spongiform encephalopathy, cerebral amyloid angiopathy, Parkinson's disease, frontal temporal dementia, Pick's disease, amyotrophic lateral sclerosis, Huntington's disease and Creutzfelds-Jakob disease.

* * * * *